United States Patent
Port et al.

(10) Patent No.: US 8,722,018 B2
(45) Date of Patent: May 13, 2014

(54) METHOD FOR PREPARING NANOPARTICLES COVERED WITH A GEM-BISPHOSPHONATE STABILIZING LAYER COUPLED TO HYDROPHILIC DISTRIBUTION LIGANDS

(75) Inventors: Marc Port, Deuil la Barre (FR); Olivier Rousseaux, Senlis (FR)

(73) Assignee: Guerbet, Villepinte (FR)

( * ) Notice: Subject to any disclaimer, the term of this patent is extended or adjusted under 35 U.S.C. 154(b) by 512 days.

(21) Appl. No.: 12/681,378

(22) PCT Filed: Oct. 6, 2008

(86) PCT No.: PCT/FR2008/051802
§ 371 (c)(1),
(2), (4) Date: Apr. 14, 2010

(87) PCT Pub. No.: WO2009/053596
PCT Pub. Date: Apr. 30, 2009

(65) Prior Publication Data
US 2010/0215586 A1    Aug. 26, 2010

(30) Foreign Application Priority Data
Oct. 5, 2007   (FR) ..................................... 07 58103

(51) Int. Cl.
*A61B 5/055* (2006.01)
(52) U.S. Cl.
USPC .......................................... 424/9.32; 424/9.3
(58) Field of Classification Search
None
See application file for complete search history.

(56) References Cited

U.S. PATENT DOCUMENTS

| 5,916,539 | A | 6/1999 | Pilgrimm | |
|---|---|---|---|---|
| 2003/0229280 | A1 | 12/2003 | Greb et al. | |
| 2004/0253181 | A1* | 12/2004 | Port et al. | 424/9.3 |
| 2006/0239926 | A1* | 10/2006 | Port et al. | 424/9.363 |

FOREIGN PATENT DOCUMENTS

| WO | 2004/058275 A | 7/2004 |
|---|---|---|
| WO | WO 2007077240 A2 * | 7/2007 |
| WO | 2009/053597 A | 4/2009 |

OTHER PUBLICATIONS

Wang, Ling et al: "A Biocompatible Method of Decorporation: Bisphosphonate-Modified Magnetite Nanoparticles to Remove Uranyl Ions from Blood", Journal of the American Chemical Society, 2006, pp. 13358-13359, 128(41), XP002475442.
Portet, D et al: "Nonpolymeric Coatings of Iron Oxide Colloids for Biological Use as Magnetic Resonance Imaging Contrast Agents", Journal of Colloid and Interface Science, Jul. 1, 2001, pp. 37-42, vol. 238, Academic Press, New York, NY, US, XP001162799.
International Search Report in Corresponding Application No. PCT/FR2008/051802 dated Nov. 11, 2009.

* cited by examiner

*Primary Examiner* — Michael G Hartley
*Assistant Examiner* — Sean R Donohue
(74) *Attorney, Agent, or Firm* — Young & Thompson

(57) ABSTRACT

A novel method for preparing nanoparticles for medical imaging, including a metal core, an organic stabilizing layer containing gem-bisphosphonate compounds and at least one hydrophilic biodistribution ligand.

8 Claims, No Drawings

METHOD FOR PREPARING NANOPARTICLES COVERED WITH A GEM-BISPHOSPHONATE STABILIZING LAYER COUPLED TO HYDROPHILIC DISTRIBUTION LIGANDS

The invention relates to a novel process for preparing nanoparticles for medical imaging comprising a metallic core, an organic stabilizing layer and at least one ligand for targeting a pathological tissue.

Metallic nanoparticles used in diagnostic imaging, especially in magnetic resonance imaging MRI are known, that comprise a metallic core, covered with a stabilizing organic layer coupled, where appropriate, to biological targeting ligands.

Among these nanoparticles, metallic nanoparticles commonly denoted by USPIO are especially known, which are very small particles of iron oxide, including, in particular, magnetite ($Fe_3O_4$), maghemite ($\gamma$-$Fe_2O_3$) and other magnetic mineral compounds of transition elements, having a size of less than approximately 100-150 nm.

In order to obtain colloidal solutions of magnetic particles that are stable in a physiological medium, it is necessary to condition the surface of the magnetic particles. In order to do this, the particle is covered with a stabilizing organic layer constituted of macromolecules such as carbohydrates, for instance dextran, or of small organic molecules such as carboxylic acids.

In order to obtain relevant information for medical imaging diagnosis, it is highly advantageous to couple the latter to suitable targeting ligands, so that the particles bind to and/or are recognized by target tissues or cells. This recognition may advantageously be provided using ligands that have an effect on the biodistribution of the product, for example via a phagocytosis-type mechanism of the particle by cells of the immune system such as macrophages. These ligands are, for example, hydrophilic groups such as amino alcohol groups, or compounds of polyethylene glycol (PEG) type.

Document WO 2004/058275 describes the synthesis of compounds using, as a stabilizing/attachment layer, a layer of gem-bisphosphonate type, and, as a ligand, among the many possible ligands, hydrophilic groups that have an effect on the biodistribution (biodistribution ligands). Compounds are in particular described that are in the form of a metallic core N covered with targeting elements of formula S—C, in which:

S is a gem-bisphosphonate group grafted to the core and of formula (I):

C is a hydrophilic ligand (coupled to the X functional group) of amino alcohol type and/or of PEG type;
where:
L represents an organic group that connects the X functional group to the gem-bisphosphonate —$CH(PO_3H_2)_2$ functional group; and
X represents a chemical functional group capable of being coupled to the hydrophilic ligand C.

For the preparation of these compounds, the prior process (used generally for USPIOs) schematically comprises the following steps:
preparation of the metallic core N of the metallic nanoparticles;
coating of the core N with the gem-bisphosphonate stabilizing layer of formula:

coupling of the particle obtained with the hydrophilic group or groups.

It is sought to improve this process in order to obtain compounds for which the amount of ligand grafted is perfectly mastered, in order to optimize and to control, with reproducibility, the degree of grafting onto the core, to avoid purification steps and to simplify the pharmaceutical control by minimizing the risks of bacterial or pyrogen contamination, and thus to obtain an efficient production of the product on an industrial scale.

Furthermore, in particular in the case of biodistribution ligands of amino alcohol or polyethylene glycol type, which are described in detail below, an additional problem lies in the required amount of ligand to be used in the process described in WO 2004/058275. Indeed, in order to obtain, in the end, a degree of coverage of targeting elements S—C that is advantageously high, especially a degree of coverage of more than 80% of the possible sites of attachment to the core, it was necessary, in this prior process, to use a large amount of ligand C in excess (it was necessary to add, to one equivalent of compound N—S [core+gem-bisphosphonate covering], around 5 equivalents of hydrophilic ligand C), hence high industrial costs. It was particularly useful to solve this problem for complex and expensive amino alcohols such as those of formula (IV), especially the amino alcohols AAG1 and derivatives thereof described below in the present application.

The applicant has succeeded in solving these technical problems by virtue of a preparation process (denoted by reverse pathway) according to which elements are prepared that are constituted by one or more hydrophilic ligands chemically coupled with organic gem-bisphosphonate linkage groups, then these elements [linkage group-ligand] are coupled to the metallic nanoparticles. The organic linkage groups will belong to or form the stabilizing (or attachment) layer.

For this purpose, the invention relates to a process for preparing metallic nanoparticles, for medical imaging in particular, comprising a metallic core N covered with an organic stabilizing layer coupled to at least one hydrophilic ligand having an effect on the stability/biodistribution of the nanoparticles, the process comprising the steps of:
a) preparing the metallic core N of the metallic nanoparticles;
b) preparing targeting/stabilizing elements of formula S—C in which:
S is a gem-bisphosphonate attachment group of formula X-L-$CH(PO_3H_2)_2$;
C is a hydrophilic biodistribution ligand advantageously chosen from amino alcohols or PEGs;
c) grafting of at least one targeting element to the core N.

For the sake of simplicity, in the application the expression "targeting elements" will be used for the expression targeting/stabilizing elements.

The expression "grafting of at least one targeting element to the core N" is understood to mean that targeting assemblies of the same structure, or several targeting assemblies for which the S groups and/or the C groups do not have the same formula, are grafted.

The advantage of having different S groups is, in particular, to be able to increase or reduce the hydrodynamic size of the contrast agent (by varying the size of the L groups), which makes it possible to help to optimize the biodistribution of the product as a function of the diagnostic indication in question.

According to some embodiments, the targeting elements are amino alcohols.

According to some embodiments, the targeting elements are PEGs.

According to some embodiments, one portion of the targeting elements are amino alcohols and another portion of the targeting elements are PEGs. The ligands may be identical or different between the targeting elements grafted.

According to some embodiments, the metallic nanoparticles obtained after grafting will thus have, for example, 10 to 90% of targeting elements with a hydrophilic ligand that has an advantageous effect on the biodistribution and/or the stability of the particle (an amino alcohol, a PEG branch, several different amino alcohols) and the balance (90 to 10%) of the targeting elements with a different ligand.

According to some embodiments, grafted to the core are, on the one hand, targeting elements S—C (bearing hydrophilic groups) and, on the other hand, stabilizing groups S that do not bear biodistribution ligands. For example, there will be 5 to 95% of S—C groups and the balance (95 to 5%) of S groups.

The table at the end of the detailed description illustrates various possibilities.

These amounts correspond to the degree of coverage of the core by the elements S or S—C (at the possible attachment sites, typically the protonated sites located at the surface of the nanoparticle). The percentages are thus expressed as the number of S—C or S molecules per number of attachment sites available on the core. Thus, for a degree of coverage of 100%, the surface of the core will be substantially completely covered with S—C and/or S elements (for example 80% of S—C groups and 20% of S groups). This degree of coverage is thus different from the degree of grafting described below.

The metallic nanoparticles have a hydrodynamic diameter of the order of 10 to 100 nm, and especially of 10 to 50 nm.

Each S group of a targeting assembly comprises at least one core linkage portion and at least one chemical functional group X for coupling with a ligand C, more specifically for covalent bonding to a reactive functional group of the ligand.

Steps a) and b) may be carried out in any order but before step c).

The assembly of the S groups grafted to the core N constitutes the attachment (stabilizing) layer. The degree of grafting (molar percentage of compound S—C and/or S per mole of iron; the degree of grafting is determined from phosphorus assays) of the targeting elements S—C and/or S to the core N is typically between 0.5 and 10%, especially 1 to 5%, for example 1, 2, 3, 5 or 10%, for a crystal size of the core of the order of 7-8 nm.

According to some embodiments, in addition to the targeting elements S—C, groups are also grafted that have an effect on the stability of the nanoparticle, for example hydroxy-monocarboxylic acids, for example chosen from the following: gluconic acid, oxalic acid, mandelic acid, 4-hydroxy-3-methoxymandelic acid, lactobionic acid, alpha-hydroxyhippuric acid, methyl-2-hydroxybutyric acid, glycolic acid, N-acetylneuraminic acid, or phosphoenolpyruvic acid.

Thus, very advantageously, it is possible to perfectly control the degree of grafting of the nanoparticles with compounds that bear ligands, which is very useful for the cost, the analysis and the characterization and the control of the physiological effectiveness of the product. The manufacture of the targeting elements S—C is furthermore completely controlled, in particular their purity before grafting, which is important for industrial manufacture.

The core N will now be described more precisely. The metallic core of the nanoparticles prepared is typically composed, completely or partly, of iron hydroxide; hydrated iron oxide; mixed iron oxides such as mixed oxides of iron with cobalt, nickel, manganese, beryllium, magnesium, calcium, barium, strontium, copper, zinc or platinum; or of a mixture of the latter. The term "ferrite" denotes the iron oxides of general formula $[xFe_2O_3.yMO_z]$, where M denotes a metal that can be magnetized under the effect of a magnetic field such as Fe, Co, Ru, Mg or Mn, it being possible for the magnetizable metal to optionally be radioactive. Preferably, the magnetic particles of the compositions of the invention comprise a ferrite, especially maghemite ($\gamma$-$Fe_2O_3$) and magnetite ($Fe_3O_4$), or else ferrites mixed with cobalt ($Fe_2CoO_4$) or with manganese ($Fe_2MnO_4$). The core of the nanoparticle was rendered acid to facilitate the coupling of the S—C elements. The process for preparing the acid core (with a step using nitric acid) is described in detail in document WO 2004/058275 (US 2004/253181, especially paragraphs 331 to 339, page 19). It is recalled that this process with an acidification step (at a highly acidic pH—typically between 1 and 3) before the attachment of the S and/or S—C groups, makes it possible to obtain particularly advantageous particles, the polydispersity of which is completely controlled and which are in a stable colloidal solution.

The L groups will now be described. Preferably, the L linkage group is a divalent group, preferably chosen from:
- an aliphatic; alicyclic; alicyclic-aliphatic; aromatic; or aromatic-aliphatic group, said aliphatic, alicyclic and aromatic groups possibly being optionally substituted with a methyl, hydroxy, methoxy, acetoxy or amido group or a chlorine, iodine or bromine atom;
- an -$L_1$-NHCO-$L_2$ group where $L_1$ and $L_2$ are either identical or different and represent an aliphatic; alicyclic; aromatic; alicyclic-aliphatic or aromatic-aliphatic group, said groups possibly being optionally substituted with a methyl, hydroxy, methoxy, acetoxy or amido group or a chlorine, iodine or bromine atom.

An aliphatic group denotes here a linear or branched hydrocarbon-based chain preferably comprising from 1 to 16 carbon atoms, better still from 1 to 6 carbon atoms. Preferably, the aliphatic group denotes an alkyl group. Examples thereof are especially methyl, ethyl, propyl, isopropyl, butyl, tert-butyl, isobutyl, pentyl and hexyl radicals.

The term "alicyclic" denotes a cyclic hydrocarbon-based chain preferably comprising from 3 to 8 carbon atoms, preferably a cycloalkyl group. By way of example, mention will especially be made of cyclopropyl and cyclohexyl.

The term "aromatic" represents an aromatic monocyclic or polycyclic hydrocarbon-based group preferably comprising from 5 to 20, better still from 6 to 18, carbon atoms. Examples thereof are especially phenyl and 1-naphthyl or 2-naphthyl radicals. According to one particular variant, an "aromatic" group within the meaning of the invention may incorporate one or more heteroatoms such as sulfur, oxygen or nitrogen. In this particular case, the "aromatic" group denotes a monocyclic or polycyclic heteroaromatic group.

The "aliphatic-alicyclic" and "aliphatic-aromatic" groups represent aliphatic chains corresponding to the aforementioned definition, substituted respectively with an alicyclic or aromatic group as defined above. By way of example of an aliphatic-aromatic group, mention may especially be made of benzyl.

According to one preferred variant, L represents an optionally substituted phenylene group, the X and gem-bisphosphonate groups possibly being in the ortho, meta or para position.

According to one particularly preferred embodiment, L represents a substituted or unsubstituted aliphatic group and more preferably a —$(CH_2)_p$— group, where p is an integer from 1 to 5.

According to another preferred embodiment, L represents an $L_1$-CONH-$L_2$ group and more preferably a —$(CH_2)_n$—NHCO—$(CH_2)_m$— group where n and m represent an integer from 0 to 5.

The X end of the gem-bisphosphonate compound of formula (I) is chosen so that it is capable of reacting and of forming a covalent bond with a functional group present on the biovector. For more information concerning these couplings, reference may especially be made to the work *Bioconjugate techniques*, Greg T. Hermanson, 1995, Publisher: Academic, San Diego, Calif.

As preferred X groups, mention may especially be made of:
—COOH,
—$NH_2$, —NCS, —NH—$NH_2$, —CHO, alkylpyrocarbonyl (—CO—O—CO-alk), acylazidyl (—CO—$N_3$), iminocarbonate (—O—C(NH)—$NH_2$), vinylsulfuryl (—S—CH=$CH_2$), pyridyldisulfuryl (—S—S-Py), haloacetyl, maleimidyl, dichlorotriazinyl, halogen,
the group of formula:

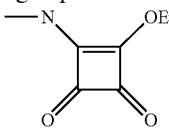

the —COOH and —$NH_2$ groups being particularly preferred.

The term "alk" denotes, within the meaning of the present description, a $C_1$-$C_6$ alkyl radical, the term "Py" denoting, for its part, a pyridyl radical.

The maleimidyl radical denotes a cyclic radical of formula:

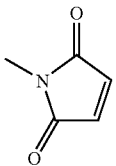

The dichlorotriazinyl radical denotes a radical of formula:

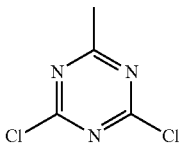

Among the halogen groups, mention may especially be made of chlorine, bromine, fluorine and iodine, chlorine and bromine being particularly preferred.

The term "haloacetyl", within the meaning of the present description, is understood to mean an acetyl radical $CH_3$—CO—, one of the hydrogen atoms of which is substituted with a halogen atom, said halogen atom being as defined above.

Preferably, X represents a —COOH or —$NH_2$ group and L a substituted or unsubstituted aliphatic group, better still a —$(CH_2)_p$— group, where p is an integer from 1 to 5.

The compound of formula (Ia):

HOOC—$(CH_2)_2$—CH$(PO_3H_2)_2$     (Ia)

is most particularly preferred.

According to another preferred embodiment, L represents an $L_1$-CONH-$L_2$ group and more preferably a —$(CH_2)_n$—NHCO—$(CH_2)_m$— group where n and m represent an integer from 0 to 5 and X represents —COOH or —$NH_2$.

Of course, also falling within the context of the invention is the coupling of the X functional group and of the biovector in an indirect manner, that is to say via a homobifunctional or heterobifunctional reagent. By way of illustration of the homobifunctional reagent, glutaraldehyde may be suitable for carrying out the coupling, for example, of an X=$NH_2$ functional group with an —$NH_2$ functional group of the biovector.

According to one preferred variant of the invention, the X functional groups form a covalent bond $L_3$ with the biovector, of the type:
—CONH—, —COO—, —NHCO—, —OCO—, —NH—CS—NH—, —C—S—, —N—NH—CO—, —CO—NH—N—, —$CH_2$—NH—, —N—$CH_2$—, —N—CS—N—, —CO—$CH_2$—S—, —N—CO—$CH_2$—S—, —N—CO—$CH_2$—$CH_2$—S—, —CH=NH—NH—, —NH—NH=CH—, —CH=N—O—, —O—N=CH— or corresponding to the following formulae:

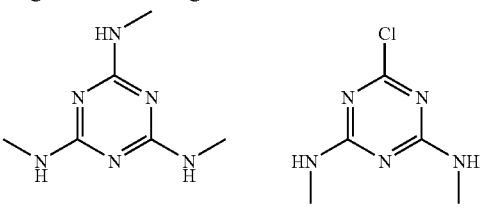

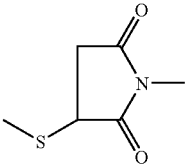

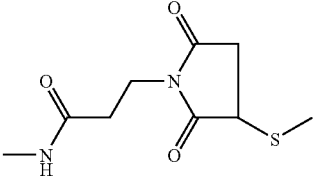

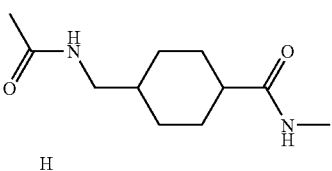

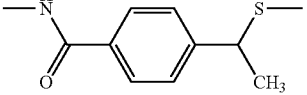

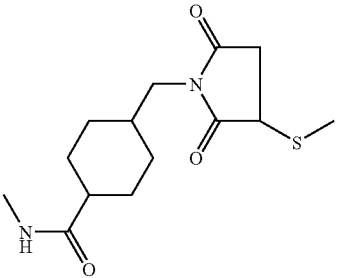

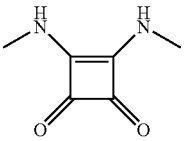

All or some, and typically of the order of 50 to 100%, especially 50, 60, 70, 80, 80 or 95% of the X functional groups of the gem-bisphosphonate compound are coupled to a biodistribution ligand.

Preferably, the hydrophilic biodistribution ligand is an amino alcohol or polyethylene glycol (also known as PEG) ligand.

The term "amino alcohol" according to the present application is understood to mean a ligand comprising an amine functional group bearing at least one aliphatic hydrocarbon-based chain comprising from 2 to 10 carbon atoms, said hydrocarbon-based chain being substituted by several hydroxyl groups, especially by 4 to 10 hydroxyl groups.

According to one preferred embodiment, the amino alcohol ligands are compounds of general formula (II):

in which:

$R_1$ and $R_2$ are identical or different and represent an aliphatic hydrocarbon-based chain comprising from 2 to 6 carbon atoms, preferably substituted with 6 to 10 hydroxyl groups, or else with 4 to 8 hydroxyl groups in the case where $R_1$ and/or $R_2$ is interrupted by one or more oxygen atoms.

As an example of an amino alcohol ligand of formula (II), mention may especially be made of the ligands for which $R_1$ and $R_2$ each independently represent a —$(CH_2)$—$(CHOH)_4$—$CH_2OH$ or —$(CH_2)$—$CHOH$—$CH_2OH$ group, in particular those for which $R_1$ represents a —$(CH_2)$—$(CHOH)_4$—$CH_2OH$ or —$(CH_2)$—$CHOH$—$CH_2OH$ group and $R_2$ a —$CH_2$—$(CHOH)_4$—$CH_2OH$ group.

According to another preferred embodiment, the amino alcohol ligands are compounds of formula (IV):

IV

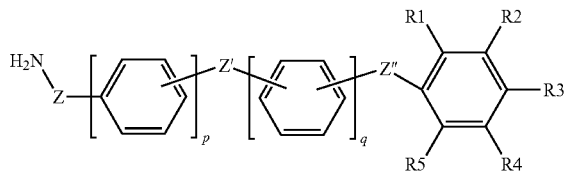

in which:

Z is a bond, $CH_2$, $CH_2CONH$ or $(CH_2)_2NHCO$;

Z' is a bond, O, S, NQ, $CH_2$, CO, CONQ, NQCO, NQ-CONQ or $CONQCH_2CONQ$,

Z" is a bond, CONQ, NQCO or $CONQCH_2CONQ$;

p and q are integers, the sum of which is equal to 0 to 3 (with, according to one advantageous variant, p=q=0);

$R_1$, $R_2$, $R_3$, $R_4$ or $R_5$ each independently represent H, Br, Cl, I, $CONQ_1Q_2$ or $NQ_1COQ_2$;

with $Q_1$ and $Q_2$, which are identical or different, chosen from H, a $(C_1-C_8)$alkyl group that is monohydroxylated or polyhydroxylated and/or optionally interrupted by one or more oxygen atoms, so that $Q_1$ and $Q_2$ comprise, between them, from 4 to 10 OH groups;

it being understood that at least one and at most two of the groups $R_1$ to $R_5$ represents $CONQ_1Q_2$ or $NQ_1COQ_2$;

or else $R_1$, $R_3$, $R_5$ each independently represent H, Br, Cl or I and $R_2$ and $R_4$ represent:

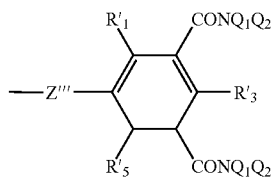

in which:

$R'_1$, $R'_3$ and $R'_5$, which are identical or different, represent H, Br, Cl or I;

$Q_1$ and $Q_2$ have the same meaning as above;

Z''' is a group chosen from CONQ, $CONQCH_2CONQ$, $CONQCH_2$, NQCONQ, $CONQ(CH_2)_2NQCO$; and Q is H or $(C_1-C_4)$alkyl, said alkyl groups possibly being linear or branched and optionally being hydroxylated.

Preferably, Z is $CH_2$.
Preferably, p=q=0.
Preferably, Z" is CONH.
Preferably, $R_2$ and $R_4$ represent $CONQ_1Q_2$.
Preferably, $R_1$, $R_3$, $R_5$ represent Br.
Preferably, $Q_1$ and $Q_2$ each independently represent a —$(CH_2)$— $(CHOH)_4$—$CH_2OH$ or —$(CH_2)$—$CHOH$—$CH_2OH$ group, in particular a —$(CH_2)$—$(CHOH)_4$—$CH_2OH$ group.

According to one particularly preferred embodiment, the amino alcohol ligand of formula (IV) is the compound:

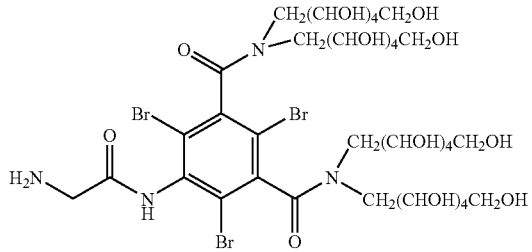

Preferably, the amino alcohol ligands according to the invention are coupled via their —NH— or —$NH_2$ amine functional group to the X functional group of the attachment groups S of formula X-L-$CH(PO_3H_2)_2$, so that the hydroxyl functional groups remain free, thus preserving their hydrophilic nature.

The expression "polyethylene glycol", within the meaning of the present application, generally denotes compounds comprising a —$CH_2$—$(CH_2$—O—$CH_2)_k$—$CH_2OR_3$ chain in which k varies from 2 to 100 (for example: 2, 4, 6, 10 or 50) and $R_3$ is chosen from H, alkyl or —(CO)Alk, the term "alkyl" or "alk" denoting a linear or branched hydrocarbon-based aliphatic group having around 1 to 6 carbon atoms in the chain.

The expression "polyethylene glycol" as used here, encompasses, in particular, the amino polyethylene glycol compounds of formula (III):

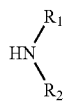

in which:

$R_1$ and $R_2$, which are identical or different, represent H, an alkyl group or a polyethylene glycol chain of formula —$CH_2$—$(CH_2$—O—$CH_2)_k$—$CH_2OR_3$, it being understood that at least one of the groups $R_1$, $R_2$ represents a polyethylene glycol chain; in which k varies from 2 to 100 (for example: 2, 4, 6, 10 or 50); and $R_3$ is chosen from H, alkyl or —(CO)Alk, the term "alkyl" or "alk" denoting a linear or branched hydrocarbon-based aliphatic group having around 1 to 6 carbon atoms in the chain.

Examples of amino polyethylene glycols are, in particular, the compounds O-(2-aminoethyl)-O'-methyl polyethylene glycol 1100, O-(2-aminoethyl)-O'-methyl polyethylene glycol 2000, O-(2-aminoethyl)-O'-methyl polyethylene glycol 750, the compounds PEG 340, PEG 750, PEG 1500, PEG 2000 for example.

It is specified that the grafting of the S—C compounds of the application to the N core is carried out by the $CH(PO_3H_2)_2$ part of the S compounds.

The applicant has noted, in particular, for the amino alcohol and/or PEG ligands that not only is the synthesis facilitated and has an improved yield, but in addition that the final product obtained corresponds very satisfactorily to the regulatory specifications and to the diagnostic use. The coverage of almost all of the core by these groups gives the product a stability and a biodistribution that are particularly advantageous for these hydrophilic ligands, in particular by improving the stealth (the product is then advantageously taken up less by the liver) and the macrophage uptake (the targeting of the macrophages is improved, with an advantage, in particular, for monitoring atheromatous plaques, ganglia and other areas of inflammation). Furthermore, the advantage of controlling the amount of ligand is understood for products having mixed coverage, for example amino alcohol ligand and PEG ligand, in order to meet the requirements of reproducibility of the production batches, of quality and of pharmaceutical safety.

Unexpectedly, the novel reverse pathway process of the applicant makes it possible to divide, by a factor of 3 to 10, the amount of biodistribution ligand, in particular of such amino alcohols. The following table illustrates this result, by taking the example of the compound from Example 14 using, as an amino alcohol, the compound from Example 4.

|  | Direct pathway (prior art) | Reverse pathway |
|---|---|---|
| Amount of amino alcohol ligand to be added in order to obtain a coverage of S—C elements greater than 90% | 5 to 10 equivalents | 1.2 to 2.2 equivalents |
| Degree of grafting (in % of amino alcohol ligand/mol of Fe) with the amino alcohol from Example 4 | 1.2% | 2% |
| Amount of amino alcohol (in mol of amino alcohol) used to obtain this degree of grafting. | 0.2 mol | 0.025 mol |

Thus, the applicant has succeeded in solving the two-fold problem of controlling the degree of grafting of the ligands and of reducing the amount of ligand to be used.

According to one particular embodiment, the process according to the invention also comprises the grafting of S—C-T elements, where C is a polyethylene glycol ligand and T represents a chromophore group.

The term "chromophore" is understood to mean a colored group, that is to say one that is capable of absorbing the energy of photons in one range of the visible spectrum whilst the other wavelengths are transmitted or scattered.

As an example of a chromophore that can be used according to the invention, mention may especially be made of 4-(amino)fluorescein hydrochloride.

The invention also relates to the use of the nanoparticles obtained by the process of the applicant for the preparation of a diagnostic or therapeutic composition. The nanoparticles are, in particular, used as a contrast agent of nanoparticle composition type as described in detail in document WO 2004/058275, for MRI imaging or an X-ray scanner.

According to some embodiments, the particles are carried in systems for the release of active principles, such as encapsulation systems of the solid lipid nanoparticle or liposome type which may also contain, in addition to the nanoparticles used as a diagnostic agent, therapeutic active principles.

Another subject of the invention are the S—C targeting elements as defined above, that can be used according to the process of the invention.

The invention is illustrated using the following detailed examples.

In what follows, the abbreviations M, M/L, theoretical M, N and M/z, $ES^+$, $ES^-$, kD and TLC have the same meanings as in document WO 2004/058275 (US 2004/253181):

M or M/L: molar concentration (mol/liter).

Theoretical M: theoretical molecular mass.

N: normality.

M/z: mass-to-charge ratio determined by mass spectrometry.

$ES^+$: positive mode electrospray.

$ES^-$: negative mode electrospray.

TFA: trifluoroacetic acid.

kD: unit of molecular mass (kiloDalton).

TLC: thin layer chromatography.

Z ave: hydrodynamic diameter measured by PCS.

Poly σ: polydispersity measured by PCS.

The chemical nomenclature which follows is derived from ACD/NAME software (Advanced Chemistry Development Inc., Toronto, Canada), according to IUPAC rules.

Total Iron Assay:

The iron is assayed by atomic absorption spectroscopy (VARIAN AA10 spectrophotometer) after mineralization with concentrated HCl and dilution with respect to a standard range of ferric ions (0, 5, 10, 15 and 20 ppm).

Particle Size:

Hydrodynamic Diameter of the Grafted Particle (Z Ave)= PCS Size:

Determined by PCS (Malvern 4700 machine, 488 nm laser at 90°) on a sample diluted to ~1 millimol with water for injection, filtered through 0.22 μm.

PCS=Photon Correlation Spectroscopy Reference:

R. Pecora in *J. of Nano. Res.* (2000), 2, p. 123-131.

Diameter of the Magnetic Particle (p) (Before Grafting):

Determined by deconvolution of the magnetization curves (measurements taken on a SQUID magnetometer) at various temperatures (reference: R. W. Chantrell in *IEEE Transactions on Magnetics* (1978), 14(5), p. 975-977).

Structural Analyses:

By mass spectroscopy (MICROMASS VG Quattro II machine) with an electrospray source.

EXAMPLE 1

A solution of 36 g (0.181 mol) of $FeCl_2.4H_2O$ and 20 ml of 37% HCl in 150 ml of $H_2O$ is introduced into a mixture consisting of 3 liters of water and 143 ml (0.302 mol) of 27% $FeCl_2$. 250 ml of 25% $NH_4OH$ are introduced rapidly with vigorous stirring. The mixture is stirred for 30 min. The liquors are removed by magnetic separation. The ferrofluid is washed 3 times consecutively with 2 liters of water. The nitric ferrofluid is stirred for 15 min with 200 ml of $HNO_3$ [2M], and the supernatant is removed by magnetic separation. The nitric ferrofluid is brought to reflux with 600 ml of water and 200 ml of $Fe(NO_3)_3$ [1M] for 30 min. The supernatant is removed by magnetic separation. The nitric ferrofluid is stirred for 15 min with 200 ml of $HNO_3$ [2M], the supernatant being removed by magnetic separation. The nitric ferrofluid is washed 3 times with 3 liters of acetone, and is then taken up with 400 ml of water. The solution is evaporated under vacuum until a final volume of 250 ml is obtained.

| Concentration M/L | Z ave nm | Poly σ | Diameter SQUID | Ms emu/cm³ |
|---|---|---|---|---|
| 4.85 | 40 nm | 0.22 | 8.5 nm | 275 |

EXAMPLE 2

108 g (0.543 mol) of $FeCl_2.4H_2O$ in 450 ml of $H_2O$ is introduced into a solution of 4 liters of water and 429 ml (0.906 mol) of 27% $FeCl_3$. 750 ml of 25% $NH_4OH$ are introduced rapidly with stirring (1200 rpm). The mixture is stirred for 30 min. The liquors are removed by magnetic separation. The ferrofluid is washed twice consecutively with 3 liters of water. The nitric ferrofluid is stirred for ¼ h with 3 liters of $HNO_3$ [2M], and the supernatant is removed by magnetic separation. The nitric ferrofluid is brought to reflux with 1300 ml of water and 700 ml of $Fe(NO_3)_3$ [1M] for 30 min (600 rpm). The supernatant is removed by magnetic separation. The nitric ferrofluid is stirred for 15 min with 3 liters of $HNO_3$ [2M], the supernatant being removed by magnetic separation.

The nitric ferrofluid is washed 3 times with 3 liters of acetone, and is then taken up with 600 ml of water. The solution is evaporated under vacuum until a final volume of 250 ml is obtained.

| % yield | Concentration M/L | Z ave (nm) | Poly σ |
|---|---|---|---|
| 81.8 | 4.45 | 31.3 | 0.21 |

200 ml of the preceding solution are stirred in 2.4 liters of $HNO_3$ for 4 hours. The supernatant is removed by magnetic separation. The nitric ferrofluid is washed twice with 3 liters of acetone, and is then taken up with 400 ml of water. The solution is evaporated under vacuum until a final volume of 250 ml is obtained.

| % yield | Concentration M/L | Z ave (nm) | Poly σ |
|---|---|---|---|
| 77 | 2.742 | 23.3 | 0.20 |

EXAMPLE 3

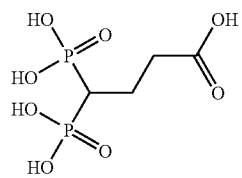 [SMILES: O=C(O)CCC(P(=O)(O)O)P(=O)(O)O]

Step a: Diethyl-1-[diethoxyphosphoryl]vinyl phosphonate 13 g (0.433 mol) of paraformaldehyde and 10 ml (0.097 mol) of diethylamine are dissolved under hot conditions in 250 ml of methanol. 24 g ($8.67 \times 10^{-2}$ mol) of diethyl[diethoxyphosphoryl]methyl phosphonate are then added. The mixture is brought to reflux for 24 hours. The reaction medium is concentrated under vacuum. The concentrate is taken up twice with 250 ml of toluene and is then concentrated under vacuum. The oil obtained is dissolved in 125 ml of toluene. 0.14 g of para-toluenesulfonic acid are added. The mixture is brought to reflux for 24 hours with a Dean-Stark trap and is then concentrated to dryness under vacuum. The product is extracted with 500 ml of $CH_2Cl_2$ and is then washed twice with 250 ml of water. The organic phase is dried over $MgSO_4$ and concentrated under vacuum. The crude product is purified on 625 g of Merck Geduran® silica gel (40-63 μm). Elution: $CH_2Cl_2$/acetone—50/50 (TLC—$SiO_2$: Rf=0.45). 18.4 g are isolated with a yield of 71%.

MS: M/z=301.4 ($ES^+$).

Step b: Diethyl 2-[2.2-bis(diethoxyphosphoryl)ethyl] malonate 1.6 g (0.01 mol) of diethyl malonate, 0.07 g (0.001 mol) of sodium ethoxide and 3 g (0.01 mol) of diethyl[diethoxyphosphoryl]vinyl phosphonate are stirred for 15 min in 15 ml of ethanol. 5 ml of a saturated $NH_4Cl$ solution are added to the ethanolic solution. The mixture is concentrated under vacuum. The residue is extracted with 30 ml of ethyl acetate and washed twice with 5 ml of water. The organic phase is dried over $MgSO_4$ and is then evaporated to dryness. The oil obtained is purified on 200 g of Merck Geduran® silica. 3.8 g are isolated with a yield of 82%.

MS: M/z=460.9 ($ES^+$).

Step c: 4,4-Diphosphonobutanoic acid 7 g ($15.7 \times 10^{-2}$ mol) of diethyl 2-[2.2-bis(diethylphosphoryl)ethyl] malonate are brought to reflux for 8 hours in 350 ml of HCl [5N]. The brown oil obtained is purified on 60 g of silanized silica gel 60 (0.063-0.200 mm) with water elution. 3.6 g are isolated with a yield of 92%.

MS: M/z=249 ($ES^+$).

EXAMPLE 4

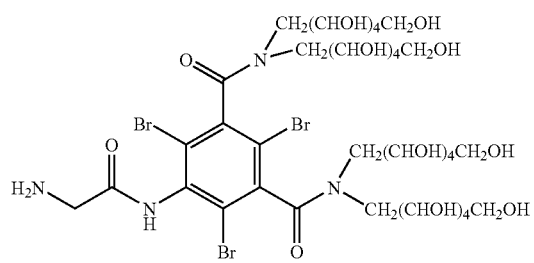

The compound (amino alcohol hydrophilic ligand) can be prepared according to the procedure described in patent: EP 0 922 700 A1.

EXAMPLE 5

600 mg of the compound prepared in Example 3, step c ($2.42 \times 10^{-3}$ M) and 3.2 g of the compound prepared in Example 4 ($4.85 \times 10^{-3}$ M) are dissolved in 20 ml of $H_2O$. The pH is adjusted to 6.2 with 0.1 N NaOH. 600 mg of EDCl ($3.13 \times 10^{-3}$ M) and 65 mg of HOBT ($4.8 \times 10^{-4}$ M) are added and the mixture is stirred at room temperature for 24 hours. The reaction medium is poured over 400 ml of IPA and stirred for 24 hours. The precipitate is filtered, then washed in ethyl ether and dried under vacuum.

The crude product is dissolved in the minimum of water by adjusting the pH to 9, then is deposited over 150 ml of Amberlite Na resin ($H^+$ form) overnight. The product is eluted with water. The good fractions are concentrated under vacuum. MS, $ES^-$: 1385.6.

EXAMPLE 6

Step a

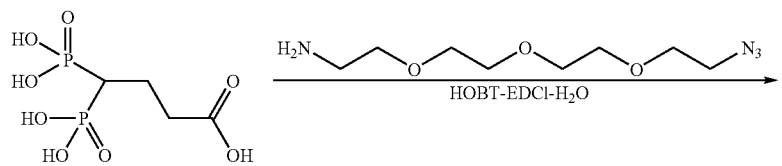

HOBT (1.72 g), then the EDCl (21.16 g) are added. The reaction medium is stirred for 24 hours at room temperature. The medium is evaporated until a final volume of around 150 ml is obtained. The pH is brought to 8 via NaOH. The solution is passed over 70 ml (30 times the theoretical amount) of Amberlite 252 Na resin ($H^+$ −1.8 meq/ml) in order to remove the excess amino PEG. Elution with $H_2O$ ($V_{recovered}$=300 ml).

The solution is evaporated until a final volume of around 150 ml is obtained.

The solution is passed over 140 ml (2 times the theoretical amount) of IRA 67 resin ($OH^-$ −1.6 meq/ml) in order to remove the excess $Cl^-$ ions. Elution with $H_2O$ ($V_{recovered}$=260 ml). The solution is evaporated until a final volume of around 100 ml is obtained. The solution is passed over 900 g of silanized silica. Elution with 2 l of $H_2O$, then with 2 l of an $H_2O/CH_3OH$ mixture (50/50).

m=28.46 g, yield=75%, LC/MS: in $ES^+$ at m/z=449.12.

Step b

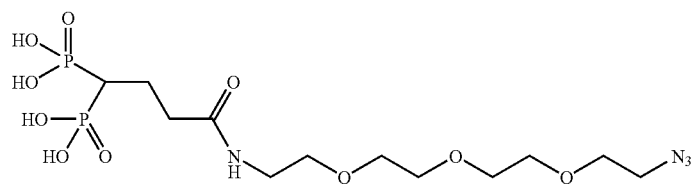

In a 500 ml three-necked flask equipped with an electrode and a magnetic stirrer, the gem-bisphosphonate (Example 3, step c, 30 g) is dissolved in $H_2O$ (250 ml). The pH is brought to 5.7 via NaOH and the amine (11-azido-3,6,9-trioxaundecan-1-amine, Fluka®, 21.8 g) is added in a single go: the

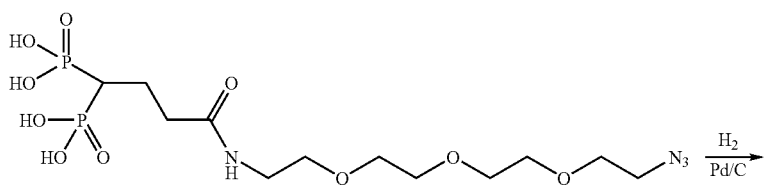

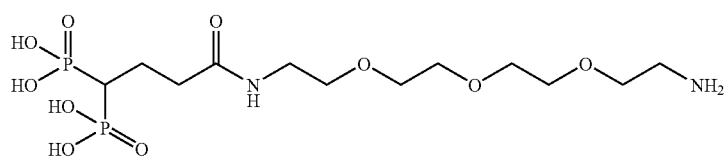

Introduced into a 1 l autoclave reactor is the azide obtained in step a (28.26 g) previously dissolved in EtOH (350 ml). The medium is acidified with a solution of HCl and four spatulas of Pd/C are introduced into the solution. The reaction medium is stirred for 4 hours at room temperature under 4 bar of hydrogen. The reaction medium is filtered over clarcel and the solution is evaporated to dryness until a straw yellow oil (31.21 g) is obtained. The product is purified by passing the solution over 200 ml of IRA 67 resin (OH⁻ −1.6 meq/ml) in order to remove the excess Cl⁻ ions. Elution with H₂O.

m=12.25 g, yield=46% (oil), LC/MS: in ES⁺ at m/z=423.12.

Step c

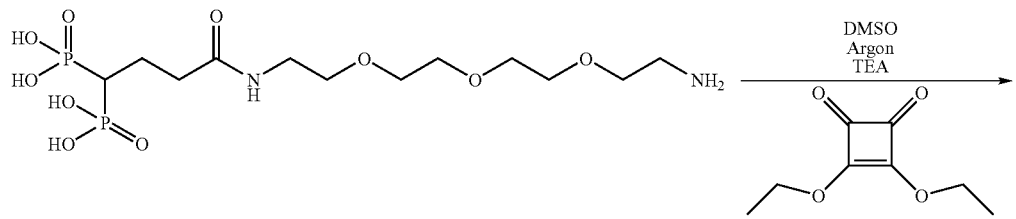

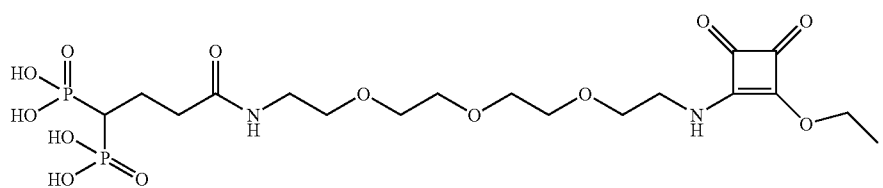

In a 250 ml three-necked flask, equipped with a magnetic stirrer, the intermediate prepared previously (12 g) is dissolved in DMSO (200 ml). Triethylamine (6696 µl), then diethyl squarate (4205 µl) are added. The medium is stirred for 72 hours at room temperature. The solution is concentrated to dryness using a vane pump until a yellow oil is obtained that is purified over silanized silica (elution with 2000 ml of H₂O, then with 2000 ml of H₂O/CH₃OH (80/20), then with 2000 ml of an H₂O/CH₃OH mixture (50/50) and with 1000 ml of CH₃OH. m=7.2 g, yield=46.4% (oil), LC/MS: in ES⁺ at m/z=547.25.

EXAMPLE 7

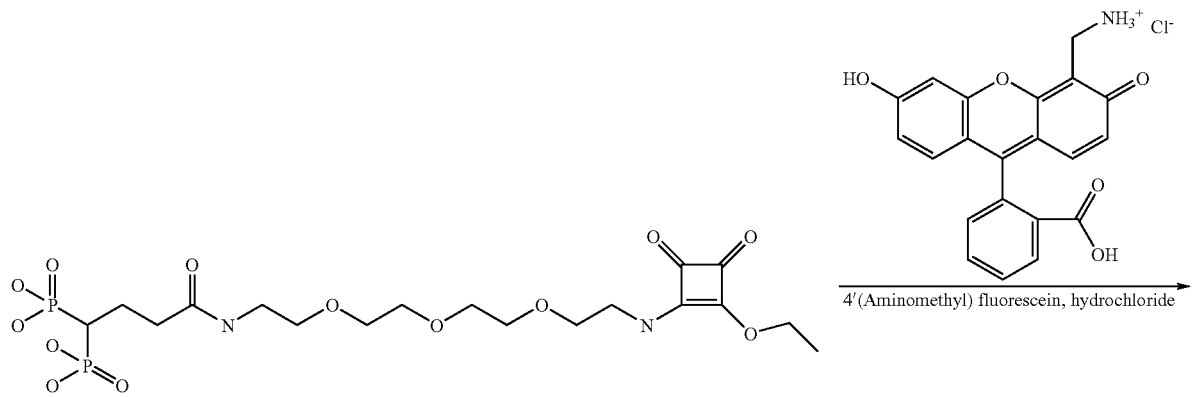

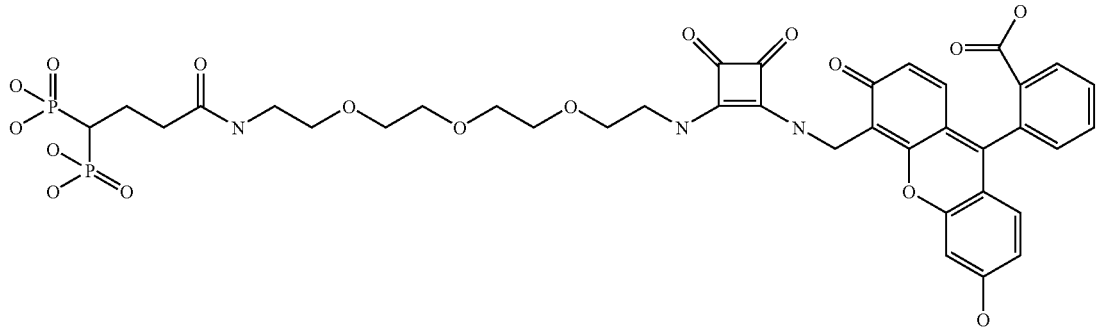

In a pill-making machine, equipped with an electrode and a magnetic stirrer, the intermediate prepared previously (Example 6, step c) (0.137 g; 2.5×10$^{-4}$ mol) is dissolved in H$_2$O (2 ml). The pH of the solution is adjusted to 7.5 with a saturated Na$_2$CO$_3$ solution. The dye (0.05 g; 1.26×10$^{-4}$ mol), previously dissolved in DMSO (1 ml), is added to the medium. The pH of the solution is equal to 6.5. The pH of the solution is brought to 8 with a saturated Na$_2$CO$_3$ solution. The solution is stirred for 48 h at room temperature. The pH of the solution is brought to 7 with a 1N hydrochloric acid solution. The solution is evaporated to dryness using a vane pump. The oil obtained is dissolved in H$_2$O (10 ml) and purified by chromatography over a cartridge of RP18 silica (25-40 μm) of 90 g. 95 mg of product are isolated with a yield of 95%. LC/MS: in ES$^-$, m/z=860.19.

EXAMPLE 8

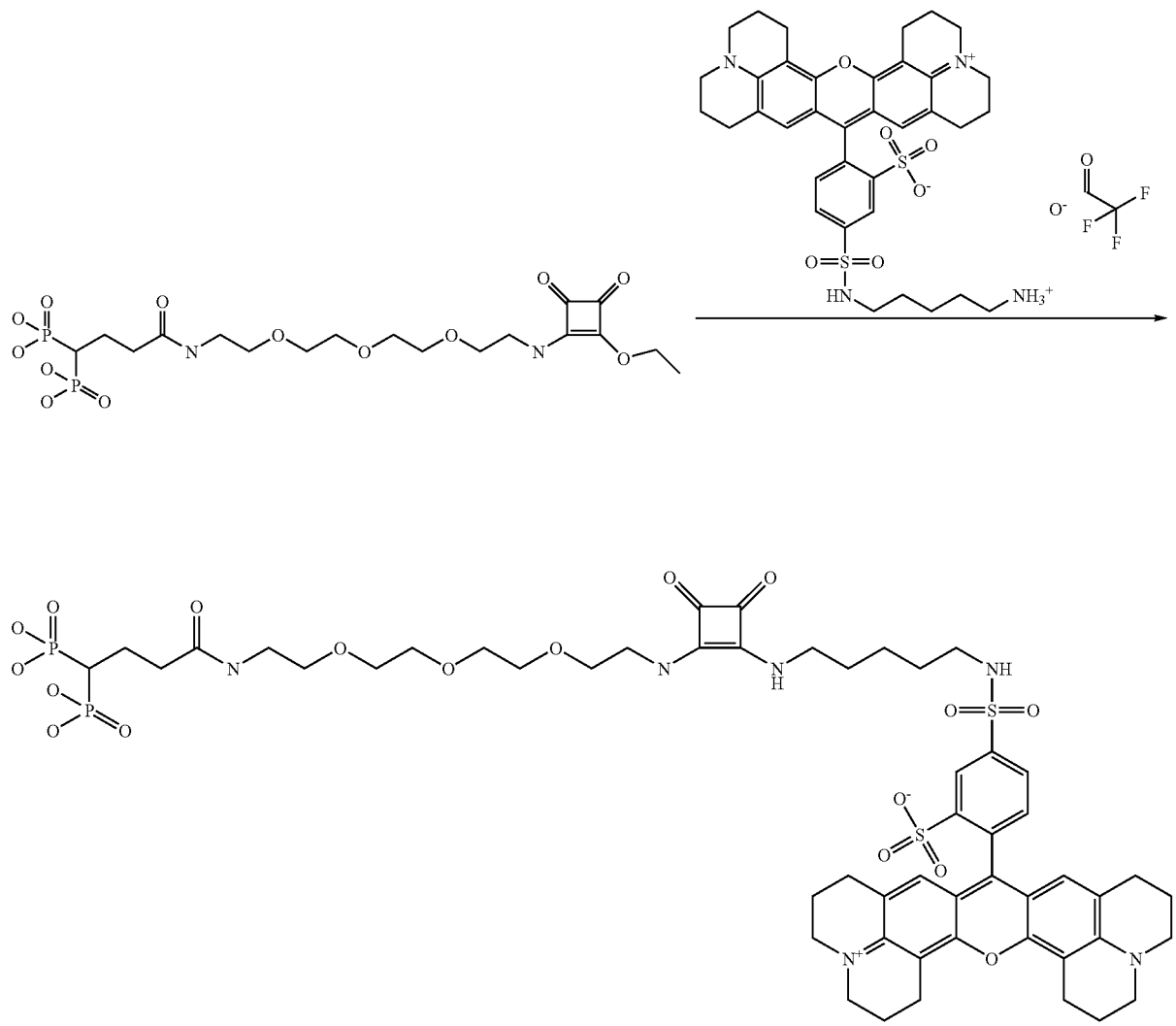

In a pill-making machine, equipped with an electrode and a magnetic stirrer, the compound prepared in Example 6, step c (0.137 g; 2.5×10⁻⁴ mol) is dissolved in H$_2$O (2 ml). The pH of the solution is adjusted to 7.5 with a saturated Na$_2$CO$_3$ solution. The dye (0.102 g; 1.26×10⁻⁴ mol), previously dissolved in DMSO (1 ml), is added to the medium. The pH of the solution is equal to 5.5. The pH of the solution is brought to 8 with a saturated Na$_2$CO$_3$ solution. The solution is stirred for 48 h at room temperature. The pH of the solution is brought to 7 with a 1N hydrochloric acid solution. The solution is evaporated to dryness using a vane pump. The oil obtained is dissolved in H$_2$O (10 ml) and purified by chromatography over a cartridge of RP18 silica (25-40 μm) of 90 g. 100 mg of product are isolated with a yield of 66%.

EXAMPLE 9

Step a

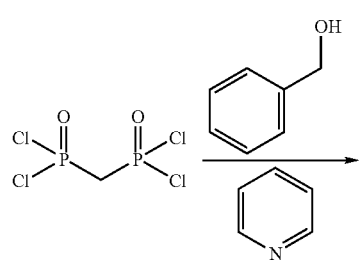

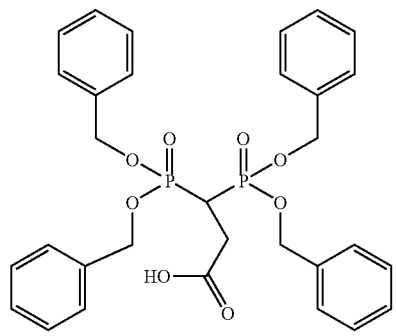

30 g of methylenebis(phosphonic dichloride) are stirred in 180 ml of toluene previously dried over molecular sieves. The temperature is kept at 0° C. A solution of 60 ml of benzyl alcohol and of 37.5 ml of pyridine is added dropwise using a syringe driver over 4 hours, it being necessary for the temperature not to exceed 0° C. The medium is stirred for 4 hours at RT. The insoluble portion is removed by filtration, and rinsed several times with toluene. The organic phase is washed 3 times with 150 ml of 2N sodium hydroxide, 250 ml of water, dried over MgSO$_4$, then concentrated. The mixture is purified over silica (eluent: heptane/ethyl acetate: 30/70).

TLC [SiO$_2$-Hept/AcOEt: 3/7—R$_f$=0.3]—yield: 60%>

LC/MS in ES⁺ 537.21

Step b

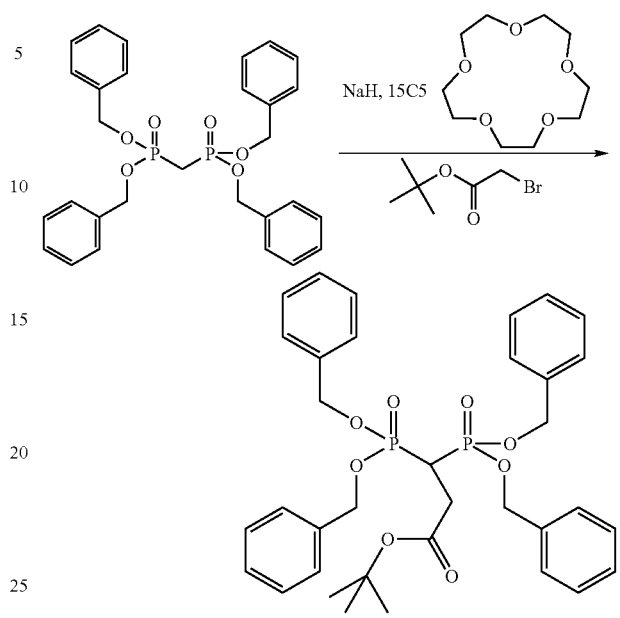

The compound prepared in step a and 15C5 are stirred in 240 ml of freshly distilled THF. 1.15 g of 60% NaH are added in small amounts to the medium. The stirring is continued for 1/2 h. t-Butyl bromoacetate, put into 25 ml of THF, is added dropwise to the ice bath. The mixture is stirred for 3 h at RT. The reaction medium is concentrated under vacuum, taken up with a saturated solution of NH$_4$Cl and extracted with 2×200 ml of CH$_2$Cl$_2$. The organic phase is dried over MgSO$_4$ and purified (Si60 cartridge: 201 nm; flow rate=20 ml/min; gradient: CH$_2$Cl$_2$/acetone)—yield: 65%.

LC/MS in ES⁺=650.65, BP-tBu: (M+1)=595.26

Step c

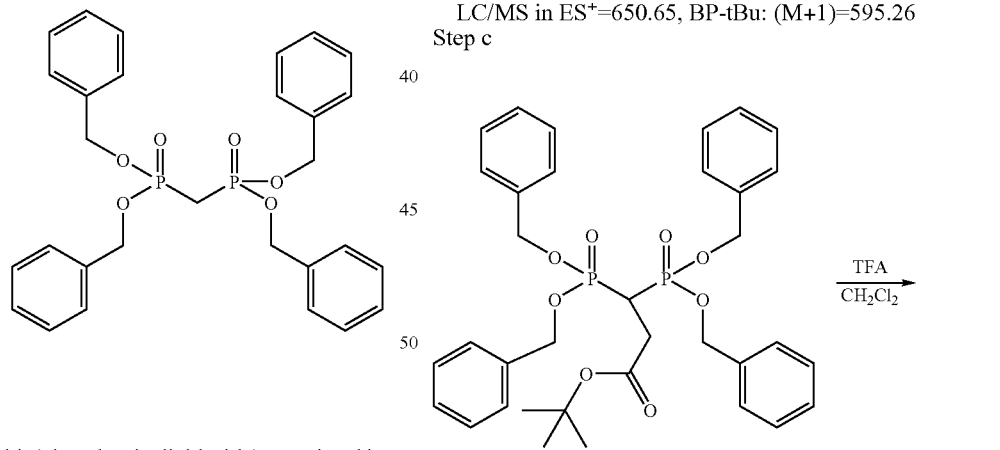

3.4 g of the compound from step b are put into solution in 35 ml of CH$_2$Cl$_2$. The solution is kept in an ice bath and 3.4 ml of TFA are added dropwise. The mixture is stirred for 4 hours at 0° C., then for 20 hours at RT. The reaction medium is evaporated under vacuum at 20° C.

The product is taken up with 20 ml of CH$_2$Cl$_2$ and washed with water then purified.

(RP 18 cartridge; detection at 201 nm; flow rate=20 ml/min; gradient: water-TFA pH=2.77/CH$_3$CN)—yield: 51%

LC/MS in ES$^+$ 595.28

EXAMPLE 10

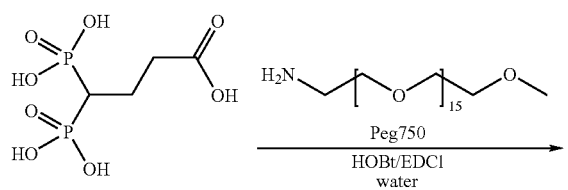

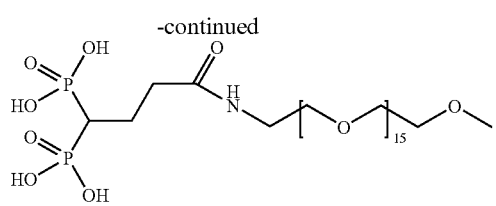

1 g of the compound obtained in step c from Example 3 (4.03×10$^{-3}$ mol) and 3.26 g of PEG750 (4.43×10$^{-3}$ mol) are dissolved in 55 ml of water. The pH is adjusted to 6.2. 272 mg of HOBT (2.01×10$^{-3}$ mol) are added and the reaction medium is stirred for 5 minutes. 1.148 g of EDCl (6×10$^{-3}$ mol) are then added and stirring is continued for 24 h. Purification over Amberlite 252Na resin with fixation of the product at pH 9. 2.3 g are obtained, i.e. a yield of 59%.

LC/MS: ES$^-$ mode, series of peaks centered about BP at 964.35.

EXAMPLE 11

Step a

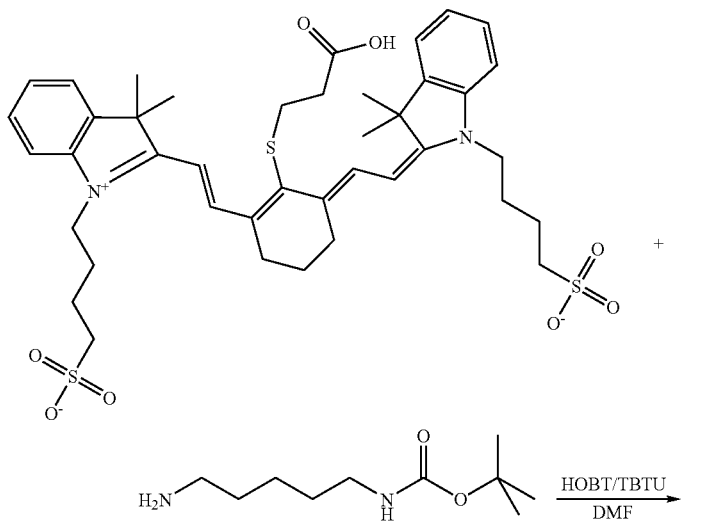

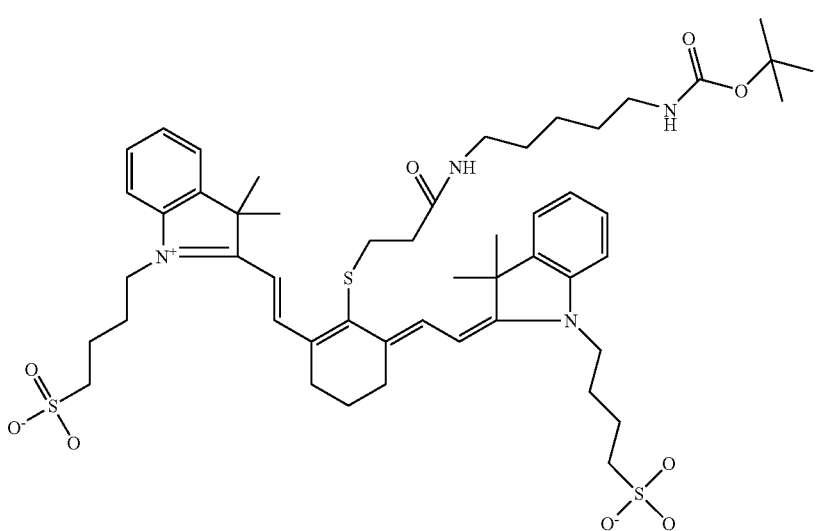

150 mg of dye ($1.88 \times 10^{-4}$ mol) are dissolved in 15 ml of DMF. Added successively are: 60 mg of HOBT ($4.44 \times 10^{-4}$ mol), 51 mg of TBTU ($1.58 \times 10^{-4}$ mol), 84 mg of tert-butyl protected diamine ($4.15 \times 10^{-4}$ mol) and 0.165 ml of DIPEA ($9.4 \times 10^{-4}$ mol). The reaction medium is stirred overnight at room temperature. Purification by reverse-phase flash chromatography. 103.4 mg of product are isolated with a yield of 55%.

LC/MS: ES$^+$ mode BP at 980.89

Step b

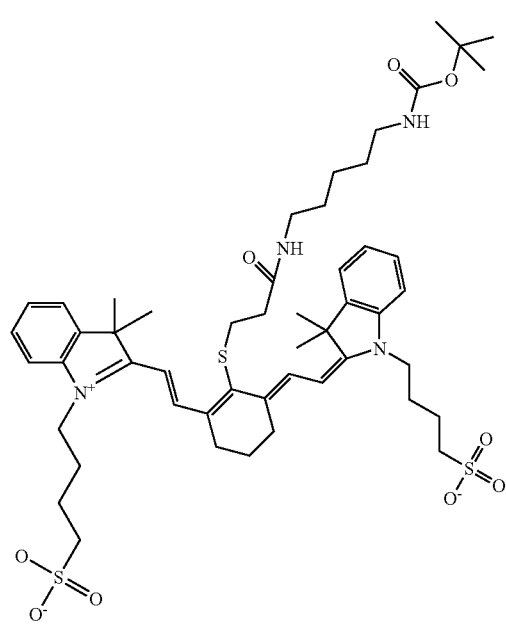

TFA →

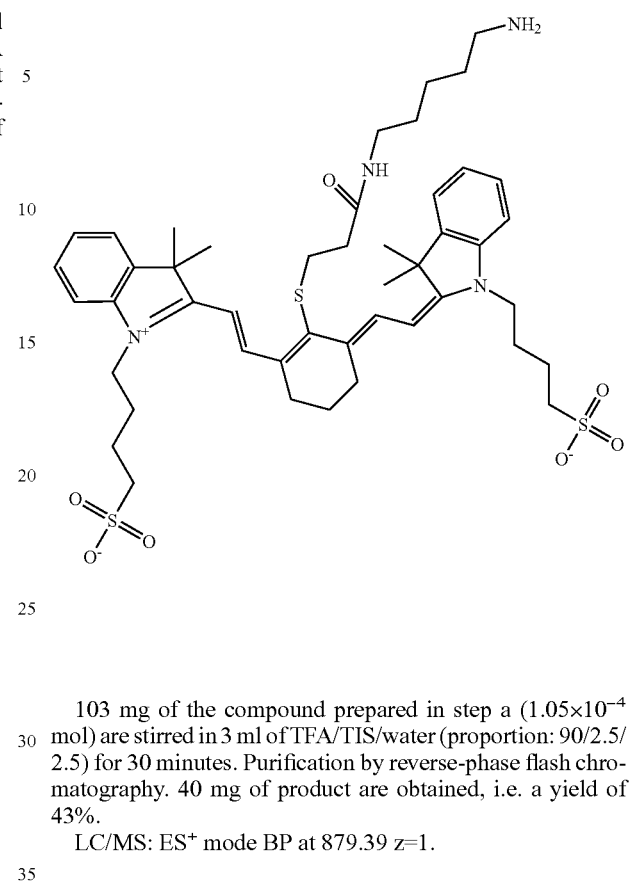

103 mg of the compound prepared in step a ($1.05 \times 10^{-4}$ mol) are stirred in 3 ml of TFA/TIS/water (proportion: 90/2.5/2.5) for 30 minutes. Purification by reverse-phase flash chromatography. 40 mg of product are obtained, i.e. a yield of 43%.

LC/MS: ES$^+$ mode BP at 879.39 z=1.

Step c

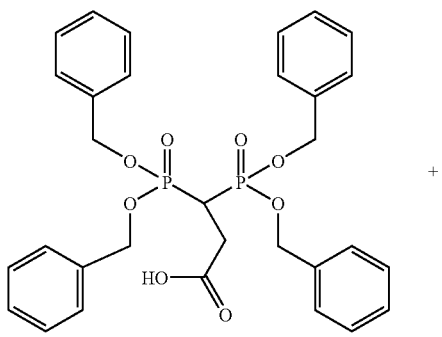

+

-continued

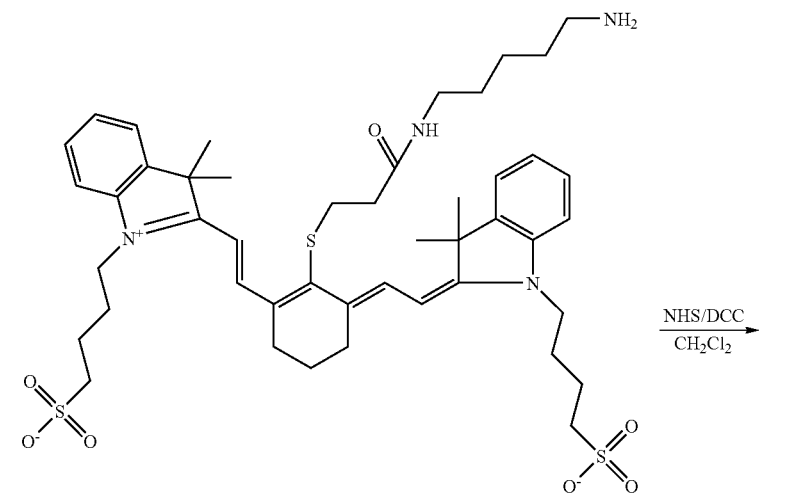

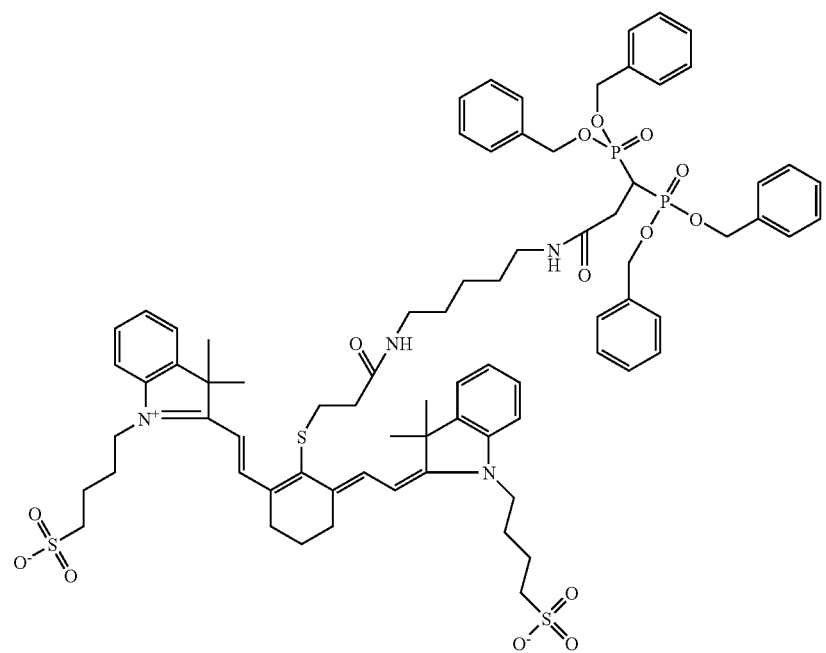

26 mg of the compound obtained in step c from Example 9 (4.37×10$^{-5}$ mol), 18 mg of DCC (8.72×10$^{-5}$ mol) and 8 mg of NHS (6.95×10$^{-5}$ mol) are stirred for 3 hours at room temperature in 5 ml of dichloromethane. The DCU is filtered. 40 mg (4.54×10$^{-5}$ mol) of the dye obtained in step b and a few drops of TEA are then added. The stirring is continued for 3 hours. Purification by reverse-phase flash chromatography. 12 mg are isolated with a yield of 20%.

LC/MS: ES$^+$ mode BP at 1457.33

Step d
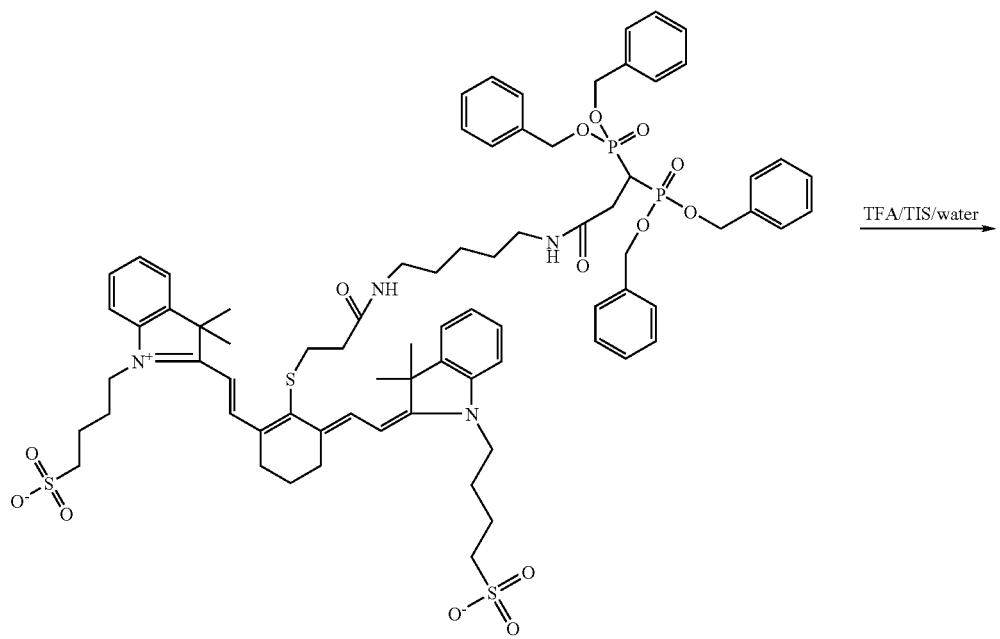
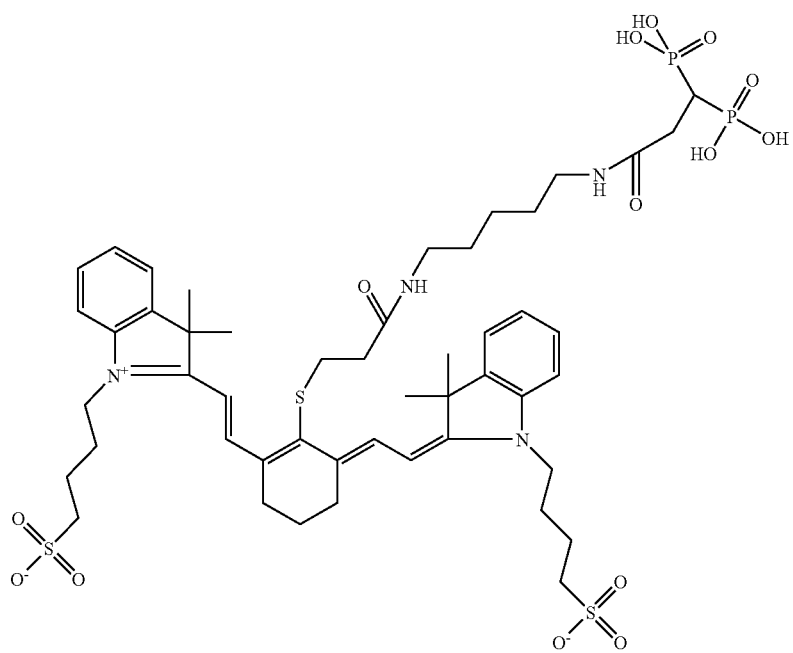
150 mg of the compound prepared in the preceding step ($1.029 \times 10^{-4}$ mol) are stirred in 4 ml of TFA/TIS/water (proportions: 95/2.5/2.5). The stirring is continued for 3 hours at room temperature. Purification by reverse-phase flash chromatography. 50 mg are obtained, i.e. a yield of 45%.
LC/MS: ES$^-$ mode BP at 1094.53 (z=1)

EXAMPLE 12

Step a

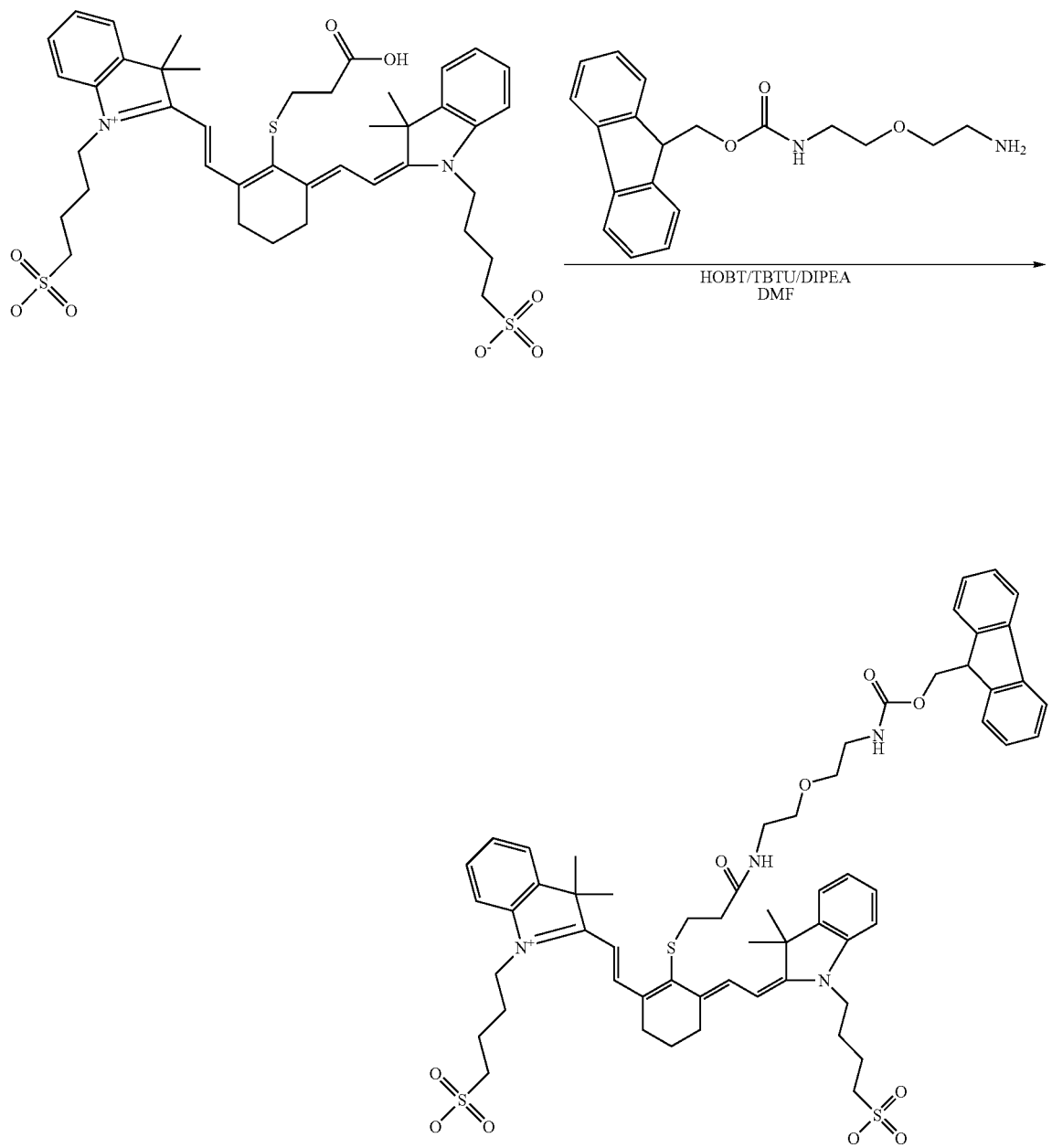

200 mg of dye ($2.51\times10^{-4}$ mol) are solubilized in 20 ml of DMF. Added successively are: 80 mg of HOBT ($5.92\times10^{-4}$ mol), 68 mg of TBTU ($2.11\times10^{-4}$ mol), 0.220 ml of DIPEA ($1.255\times10^{-3}$ mol) and 108 mg of Fmoc-aminoethoxyethylamine ($3.30\times10^{-4}$ mol). The reaction medium is stirred overnight at room temperature. Purification by flash chromatography. Water/CH$_3$CN. 178 mg of product are isolated with a yield of 65%.

LC/MS: ES$^+$ mode, BP at 1103.43 (z=1)

Step b
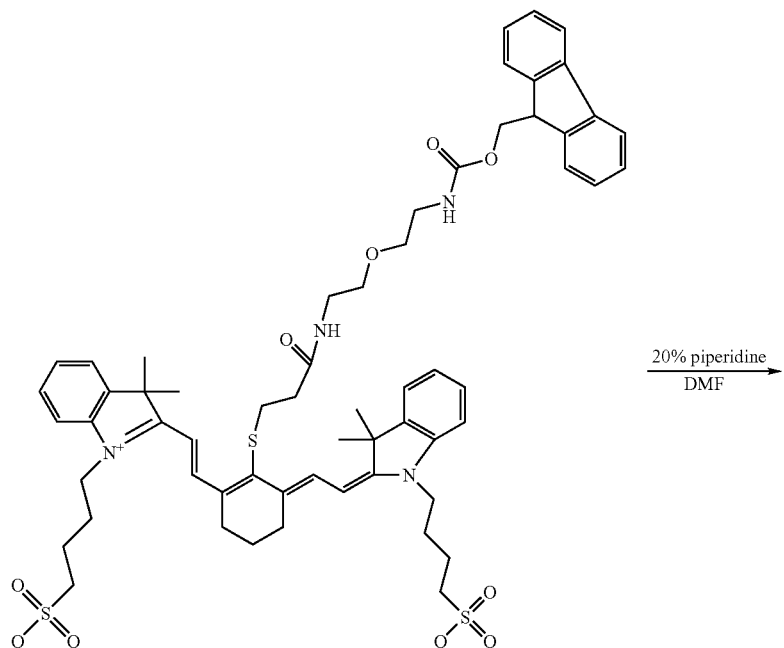
20% piperidine / DMF →
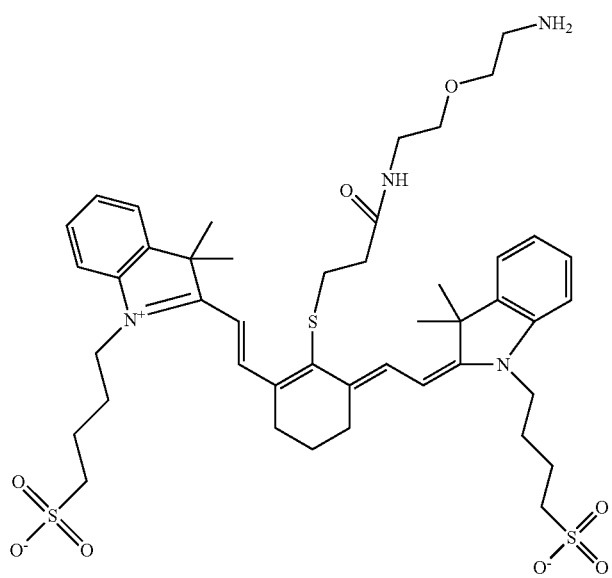
80 mg of the compound prepared in the preceding step (9.0×10$^{-5}$ mol) are put into solution in 6 ml of DMF containing 20% piperidine. The stirring is continued for 1 hour at room temperature. Purification by reverse-phase flash chromatography. 50 mg of product are obtained, i.e. a yield of 40%.
LC/MS: ES$^-$ mode, BP at 880.09 (z=1)

Step c
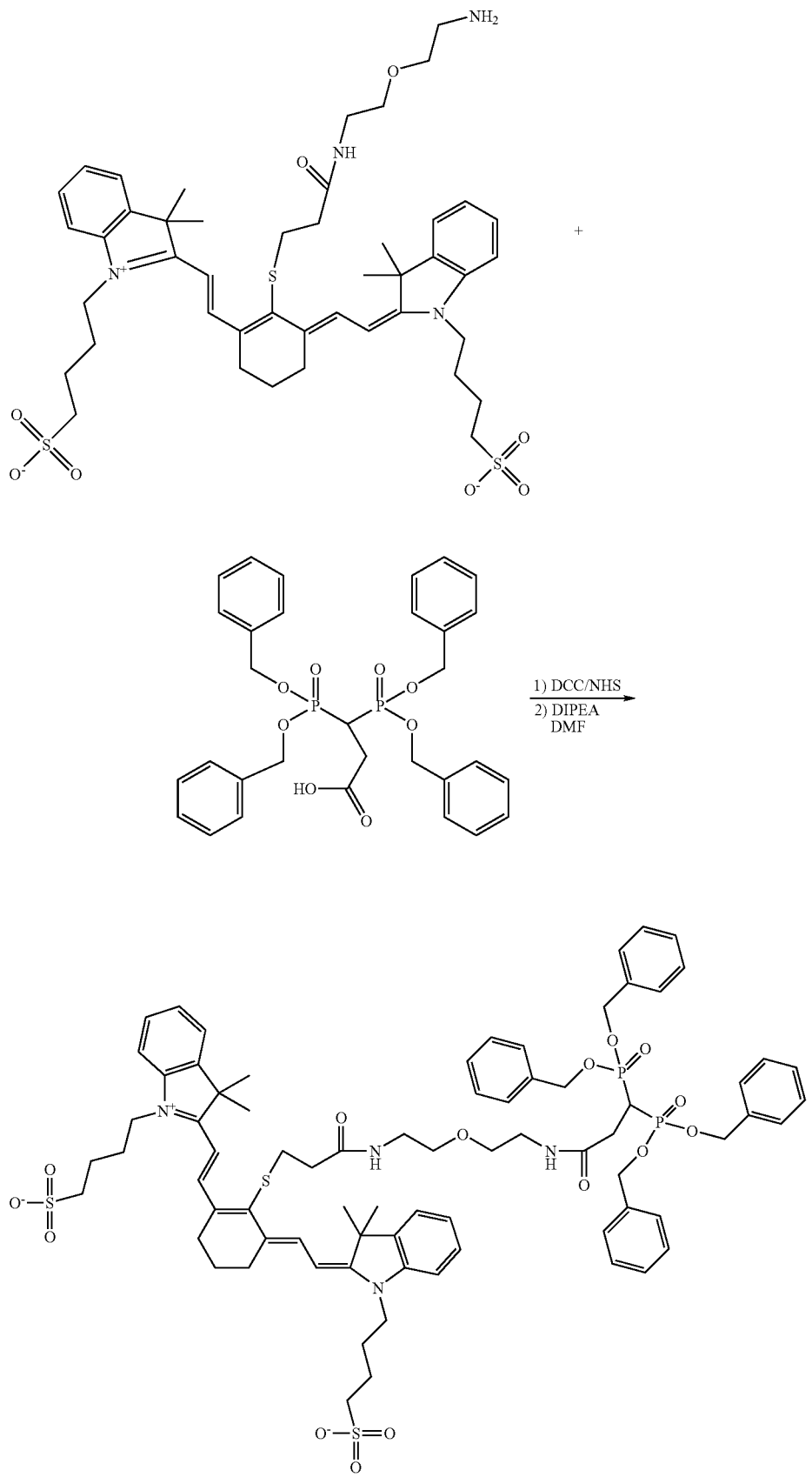

20 mg of the benzyl-containing tweezers obtained in step c from Example 9 ($3.36 \times 10^{-5}$ mol), 14 mg of DCC ($6.78 \times 10^{-5}$ mol) and 6 mg of NHS ($5.21 \times 10^{-5}$ mol) are dissolved in DMF and stirred for 3 hours at room temperature. The DCU is removed. 30 mg ($3.4 \times 10^{-5}$ mol) of the dye obtained in step b and 17 μl of DIPEA ($1.02 \times 10^{-4}$ mol) are dissolved in 1 ml of DMF; the activated ester is then added dropwise. The stirring is continued for 3 hours at room temperature. Purification by reverse-phase flash chromatography. 30 mg are obtained, i.e. a yield of 36%.

LC/MS: ES$^+$ mode, BP at 1458.90 (z=1).

Step d

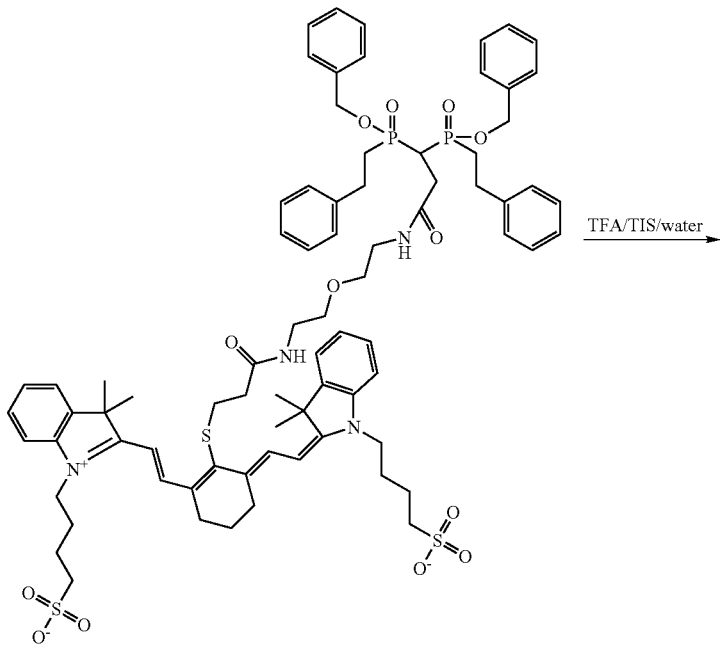

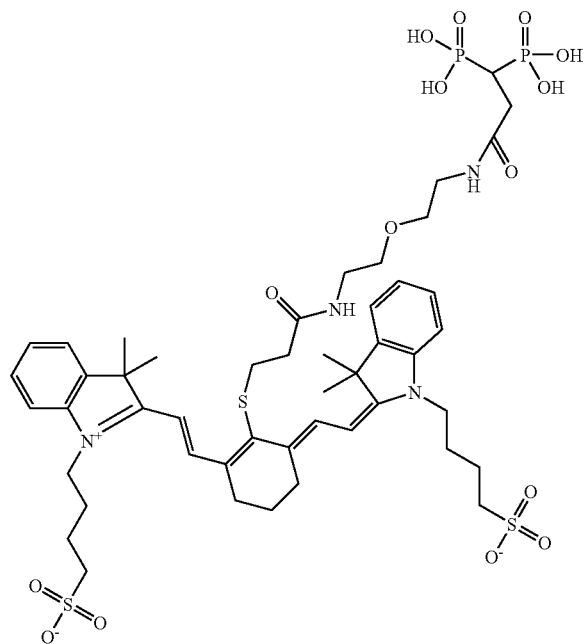

30 mg of the compound prepared in step c ($2.03 \times 10^{-5}$ mol) are dissolved in 3 ml of TFA/TIS/water (proportions: 95/2.5/2.5) for 3 h 50 min at room temperature. Purification by flash chromatography. 6 mg are obtained, i.e. a yield of 35%.

LC/MS: ES$^+$ mode, BP at 1098.21 (z=1) and 550.3 (z=2).

EXAMPLE 13

Step a

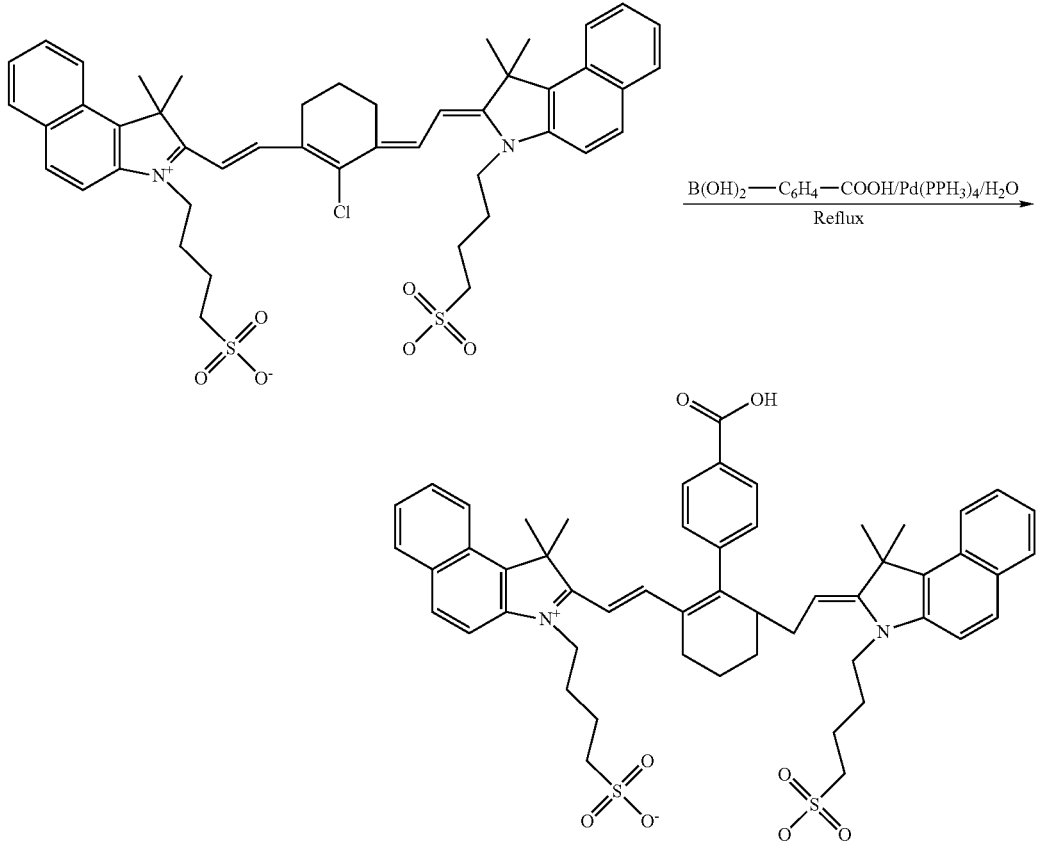

50 mg of IR820 (Aldrich®, $5.88 \times 10^{-5}$ mol) and 14.65 mg ($8.82 \times 10^{-5}$ mol) of phenylboronic acid are heated to reflux in the presence of 10.7 mg ($9.24 \times 10^{-6}$ mol) of tetrakis(triphenylphosphine)palladium and of 40.7 mg of K$_2$CO$_3$ ($2.9 \times 10^{-4}$ mol) for 24 h at 110° C. At the end of the experiment, the palladium is filtered. Purification by reverse-phase flash chromatography. 33 mg are obtained, i.e. a yield of 62%.

LC/MS: ES$^+$ mode, BP at 913.27 (z=1).

Step b

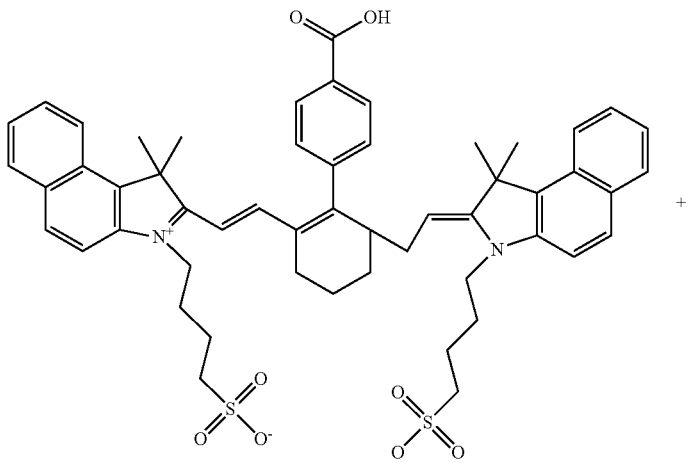

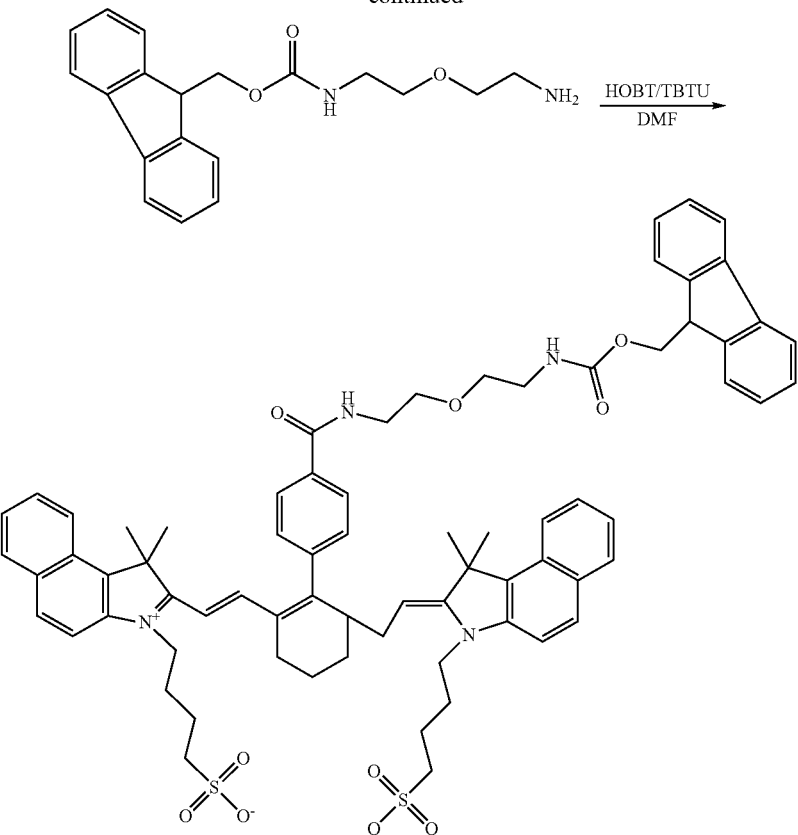
18 mg of the compound prepared in step a ($1.96 \times 10^{-5}$ mol), 7 mg of HOBT ($4.31 \times 10^{-5}$ mol), 7 mg of TBTU ($4.70 \times 10^{-5}$ mol), 10 mg of Fmoc-aminoethoxyethylamine ($2.15 \times 10^{-6}$ mol) and 11 µl of DIPEA ($9.8 \times 10^{-5}$ mol) are stirred overnight at room temperature. The reaction medium is triturated in diethyl ether (20 mg) and filtered. 13 mg of product are thus isolated with a yield of 55%.
Step c
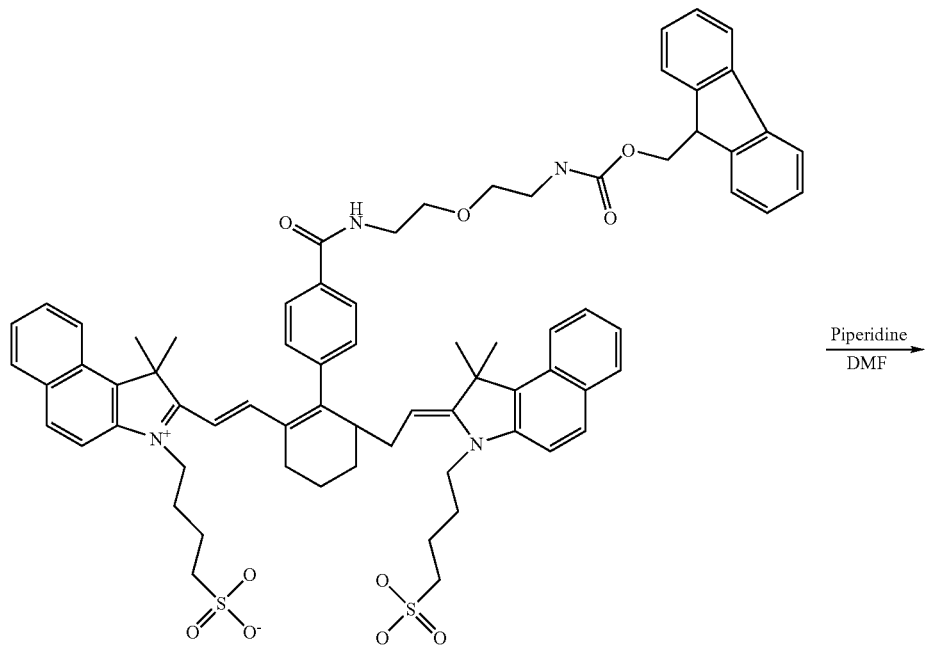

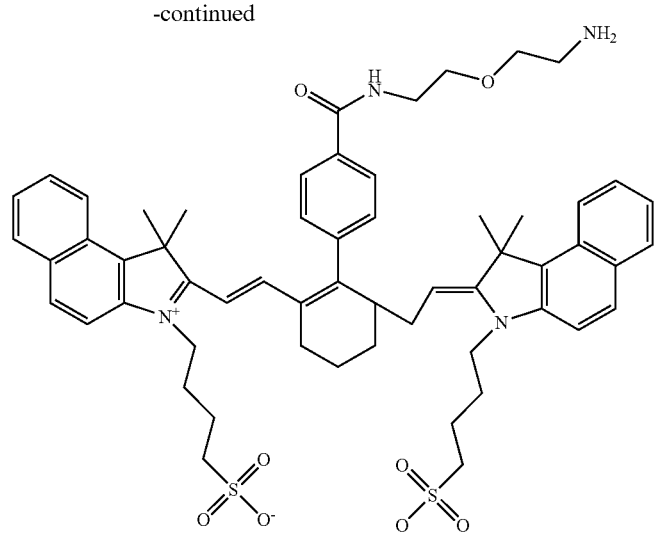
13 mg of the compound obtained in step b ($1.06 \times 10^{-5}$ mol) are stirred in DMF and 20% piperidine.
The stirring is continued for 30 minutes at room temperature. Precipitation into 20 ml of ethyl ether and stirring for 1 hour at room temperature. 4.3 mg are obtained, i.e. a yield of 40%.
Step d
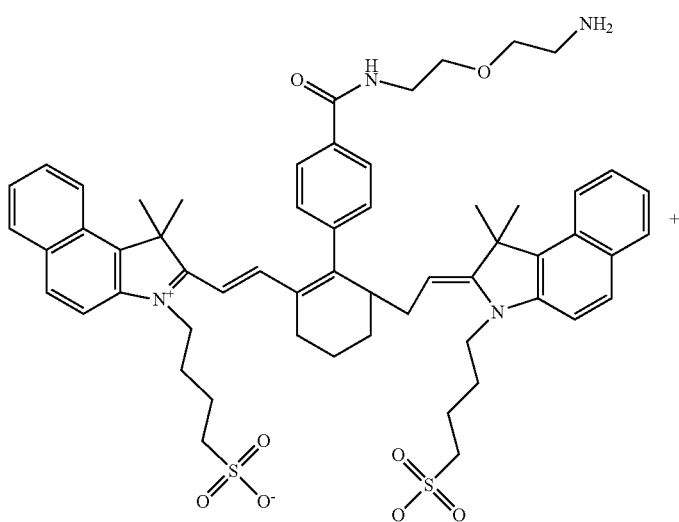
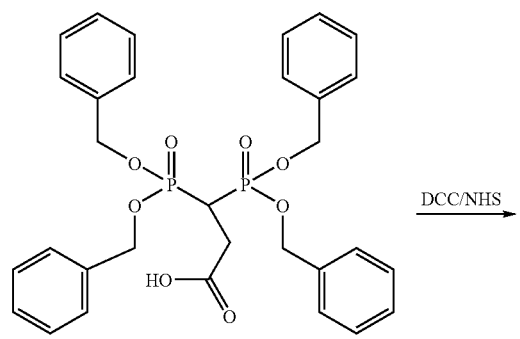

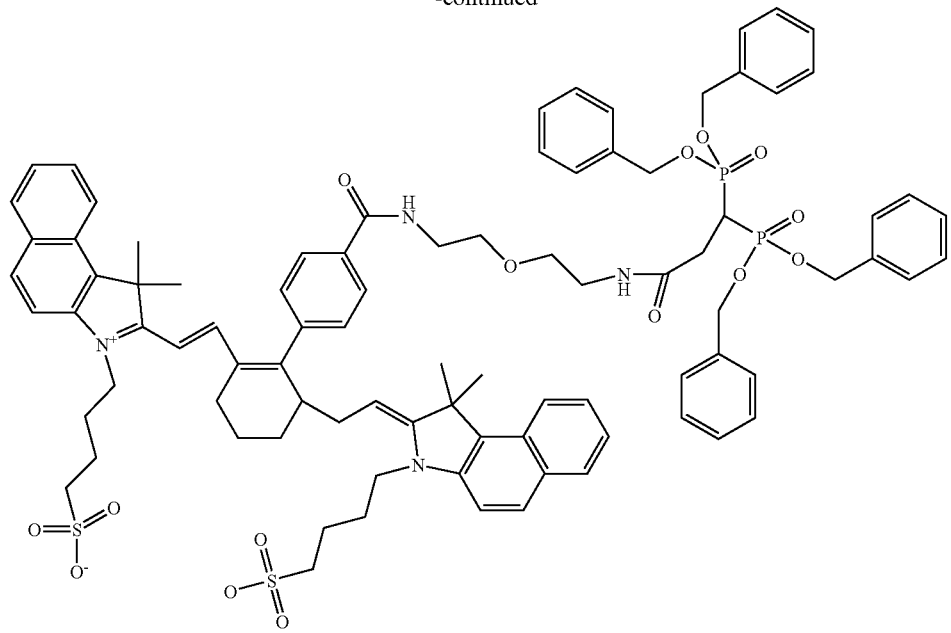

20 mg of the compound obtained in step c from Example 9 (3.36×10⁻⁵ mol), 14 mg of DCC (6.78×10⁻⁵ mol) and 6 mg of NHS (5.21×10⁻⁵ mol) are dissolved for 3 hours at room temperature. The DCU is removed. 35 mg (3.4×10⁻⁵ mol) of the dye obtained in step c and 17 µl of DIPEA (1.02×10⁻⁴ mol) are dissolved in 1 ml of DMF; the activated ester is then added dropwise. The stirring is continued for 3 hours at room temperature.

Precipitation in 50 ml of ethyl ether. 20 mg are obtained, i.e. a yield of 37%.

Step e

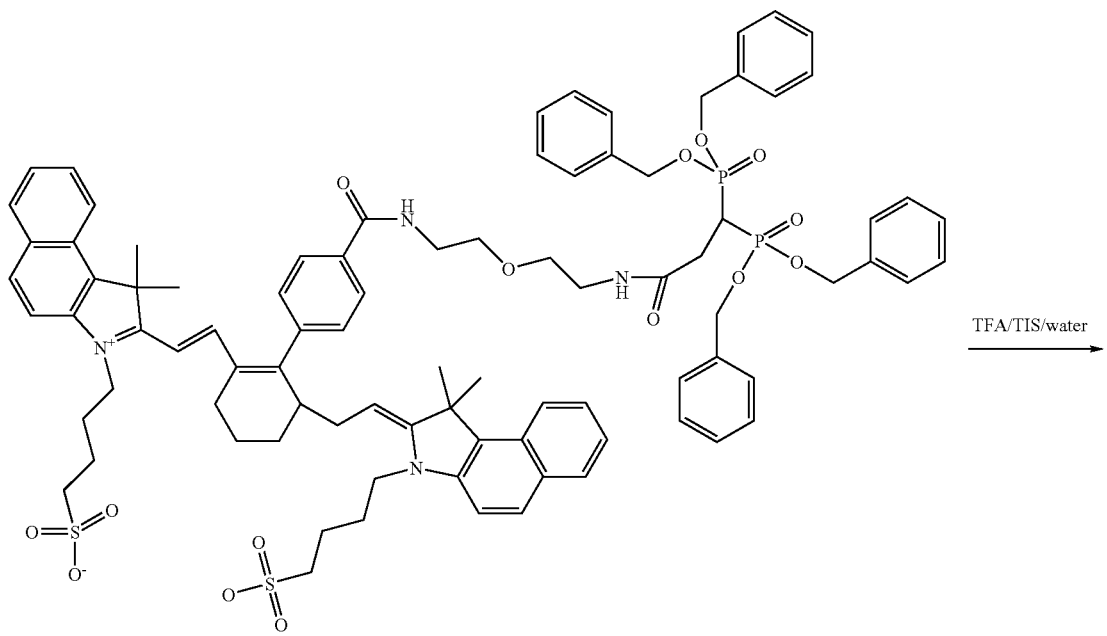

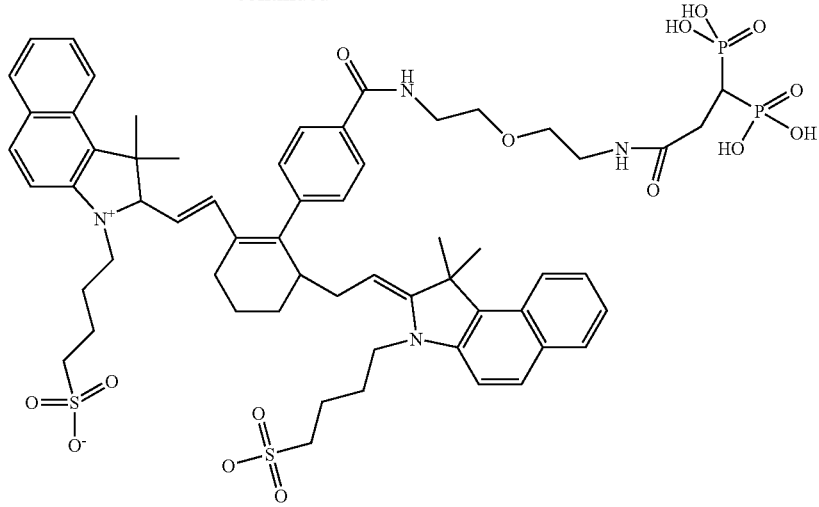

20 mg of the compound prepared in step d ($1.25 \times 10^{-5}$ mol) are stirred in 3 ml of TFA/TIS/water (95/2.5/2.5) for 3 h and at room temperature. Purification by reverse-phase flash chromatography. 4 mg are isolated, i.e. a yield of 26%.

EXAMPLE 14

60 μmol of the compound obtained in Example 5 in solution in 10 ml of water are added dropwise to a solution of 1 ml of Example 2 (acid ferrofluid) at a concentration of 2.75 M/L diluted in 100 ml of water. The mixture is stirred for 20 minutes at room temperature and the pH is adjusted to 7.2. The solution obtained is ultrafiltered through a membrane having a cut-off threshold of 30 kD. 300 ml of filtrate are removed in order to obtain a final solution of 10 ml.

[Fe]: 0.260 M/L PCS size=28 nm

Degree of grafting [amino alcohol compound/Fe]=2% mol/mol

EXAMPLE 15

3 ml of the compound described in Example 2 ([Fe]=1.336 mol/l) are diluted in 100 ml of water. Added to the solution, successively and with a delay of minutes between each addition, are a solution of 46 mg of the compound described in Example 5 in 2 ml of water, a solution of 3.85 mg of the compound described in Example 7 in 2 ml of water and finally a solution of 46 mg of the compound from Example 5 in 2 ml of water. The solution is stirred for 15 minutes at room temperature and the pH is adjusted to 7.4 with a solution of NaOH. The medium is ultrafiltered through a 30 KD membrane and the volume of the solution is brought to 20 ml for an iron concentration of 0.191 mol/l. PCS: 26.8.

EXAMPLE 16

According to the procedure from Example 16, various binary or tertiary combinations of bisphosphonate compounds in variable proportions are fixed to the particles of iron oxide described in Example 1 or 2 as summarized in the following table:

| No. | Particles | Biphosphonate 1 (% mol) | Biphosphonate 2 (% mol) | Biphosphonate 3 (% mol) | PCS size nm |
|---|---|---|---|---|---|
| 1 | Example 1 | Example 5 (40) | Example 3 (60) | — | 42 |
| 2 | Example 2 | Example 5 (60) | Example 3 (30) | Example 7 (10) | 28 |
| 3 | Example 2 | Example 5 (95) | Example 7 (5) | — | 27 |
| 4 | Example 2 | Example 5 (90) | Example 8 (10) | — | 26 |
| 5 | Example 2 | Example 5 (95) | Example 11 (5) | — | 28 |
| 6 | Example 2 | Example 10 (20) | Example 3 (80) | — | 29 |
| 7 | Example 2 | Example 10 (95) | Example 12 (5) | — | 28 |
| 8 | Example 2 | Example 10 (80) | Example 3 (15) | Example 12 (5) | 27 |
| 9 | Example 2 | Example 10 (98) | Example 13 (2) | — | 28 |
| 10 | Example 2 | Example 10 (100) | — | — | 27 |
| 11 | Example 2 | Example 5 (100) | — | — | 26 |
| 12 | Example 2 | Example 5 (96) | Example 12 (2) | Example 7 (2) | 27 |
| 13 | Example 2 | Example 5 (50) | Example 10 (50) | — | 28 |

The numbers between parentheses indicate the degree of coverage, for example for No. 1: the coverage is composed of 40% of the compound from Example 5 (amino alcohol ligand) and of 60% of the compound from Example 3 (bisphosphonate compound not connected to a ligand).

The invention claimed is:

1. A process for preparing metallic nanoparticles, the nanoparticles comprising a metallic core N covered with an organic stabilizing layer coupled to at least one hydrophilic ligand having an effect on the stability/biodistribution of the nanoparticles, the process comprising the steps of:
   a) preparing the metallic core N of the metallic nanoparticles;
   b) preparing targeting elements of formula S—C, in which:
      S is a gem-bisphosphonate attachment group of formula X-L-CH($PO_3H_2$)$_2$, and
      C is a hydrophilic biodistribution ligand selected from:
      (1) an amino alcohol of formula (II):

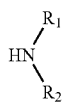

(II)

wherein,
   $R_1$ and $R_2$ idependently represent an aliphatic hydrocarbon-based chain comprising from 2 to 6 carbon atoms;
(2) an amino alcohol of formula (IV):

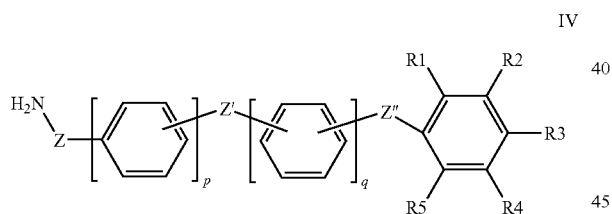

IV wherein, Z is a bond, $CH_2$, $CH_2CONH$ or $(CH_2)_2NHCO$;
Z' is a bond, O, S, NQ, $CH_2$, CO, CONQ, NQCO, NQCONQ or CONQCH$_2$CONQ,
Z" is a bond, CONQ, NQCO or CONQCH$_2$CONQ;
p and q are integers, the sum of which is equal to 0 to 3;
$R_1$, $R_2$, $R_3$, $R_4$ or $R_5$ each independently represent H, Br, Cl, I, CONQ$_1$Q$_2$ or NQ$_1$COQ$_2$;
$Q_1$ and $Q_2$, which are identical or different, are H, a (C1-C8)alkyl group that is monohydroxylated or polyhydroxylated and/or optionally interrupted by one or more oxygen atoms, so that $Q_1$ and $Q_2$ comprise, between them, from 4 to 10 OH groups;
it being understood that at least one and at most two of the groups $R_1$ to $R_5$ represents CONQ$_1$Q$_2$ or NQ$_1$COQ$_2$;
or else $R_1$, $R_3$, $R_5$ each independently represent H, Br, Cl or I and $R_2$ and $R_4$ represent:

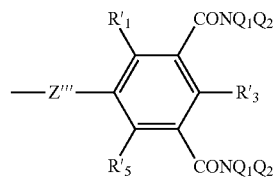

wherein R'$_1$, R'$_3$ and R'$_5$, which are identical or different, represent H, Br, Cl or I;
$Q_1$ and $Q_2$ have the same meaning as above;
Z''' is CONQ, CONQCH$_2$CONQ, CONQCH$_2$, NQCONQ, or CONQ(CH$_2$)$_2$NQCO; and
Q is H or (C$_1$-C$_4$)alkyl, said alkyl group being linear or branched and optionally being hydroxylated; and
(3) a polyethylene glycol ligand being an amino polyethylene glycol of formula (III):

in which:
$R_1$ and $R_2$, which are identical or different, represent H, an alkyl group or a polyethylene glycol chain of formula —CH$_2$—(CH$_2$—O—CH$_2$)$_k$—CH$_2$OR$_3$, it being understood that at least one of the groups $R_1$, $R_2$ represents a polyethylene glycol chain;
k varies from 2 to 100; and
$R_3$ is H, C$_1$-C$_6$ alkyl or —(CO)Alk, with "alk" denoting a C$_1$-C$_6$ alkyl group; and
c) grafting the S group of the targeting elements of formula S—C to the metallic core N;
wherein:
X represents a chemical functional group capable of being coupled to the hydrophilic biodistribution ligand C and is selected from the group consisting of: —COOH, —NH$_2$, —NCS, —NH—NH$_2$, —CHO, alkylpyrocarbonyl (—CO—O—CO-alk), acylazidyl (—CO—N$_3$), iminocarbonate (—O—C(NH)—NH$_2$), vinylsulfuryl (—S—CH=CH$_2$), pyridyldisulfuryl (—S—S-Py), haloacetyl, maleimidyl, dichlorotriazinyl, halogen, and the group of formula:

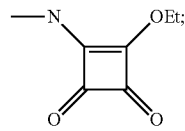

and
L represents an organic group that connects the X functional group to the gem-bisphosphonate —CH(PO$_3$H$_2$)$_2$ functional group, L being a divalent group selected from the group consisting of:
an aliphatic, alicyclic, alicyclic-aliphatic aromatic and aromatic-aliphatic group, said aliphatic, alicyclic and aromatic groups being optionally substituted with a methyl, hydroxy, methoxy, acetoxy or amido group or a chlorine, iodine or bromine atom, and
an -L$_1$-NHCO-L$_2$ group where L$_1$ and L$_2$ are either identical or different and represent an aliphatic, alicyclic, aromatic, alicyclic-aliphatic or aromatic-aliphatic group, said groups being optionally substituted with a methyl, hydroxy, methoxy, acetoxy or amido group or a chlorine, iodine or bromine atom.

2. The process as claimed in claim 1, wherein the metallic core is iron hydroxide, hydrated iron oxide, ferrite, or mixed iron oxide.

3. The process as claimed in claim 1, wherein one portion of the hydrophilic biodistribution ligand C is an amino alcohol ligand and another portion is a polyethylene glycol ligand.

4. The process as claimed in claim 1, wherein on the one hand, the S group of the targeting elements S—C are grafted to the metallic core N, and on the other hand, the attachment groups S that do not bear the biodistribution ligands (C) are grafted to the metallic core N.

5. The process as claimed in claim 1, wherein the degree of grafting of the targeting elements to the metallic core N is from 1 to 10%.

6. The process as claimed in claim 1, further comprising grafting elements S—C-T to the metallic core N, wherein C is a polyethylene glycol ligand and T represents a chromophore group.

7. The process as claimed in claim 1, wherein
C is an aminoalcohol of formula (II), and
$R_1$ and $R_2$ represent an aliphatic hydrocarbon-based chain comprising from 2 to 6 carbon atoms substituted with 6 to 10 hydroxyl groups, or else with 4 to 8 hydroxyl groups in the case where $R_1$ and/or $R_2$ is interrupted by one or more oxygen atoms.

8. The process as claimed in claim 5, wherein the degree of grafting of the targeting elements to the metallic core N is from 2 to 5%.

* * * * *

UNITED STATES PATENT AND TRADEMARK OFFICE
CERTIFICATE OF CORRECTION

PATENT NO. : 8,722,018 B2  Page 1 of 1
APPLICATION NO. : 12/681378
DATED : May 13, 2014
INVENTOR(S) : Port et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 600 days.

Signed and Sealed this
Twenty-ninth Day of September, 2015

Michelle K. Lee
*Director of the United States Patent and Trademark Office*